US012629199B2

(12) United States Patent
Batchelor et al.

(10) Patent No.: US 12,629,199 B2
(45) Date of Patent: May 19, 2026

(54) FEEDBACK CONTROL IN ELECTROSURGICAL SYSTEMS

(71) Applicant: GYRUS ACMI, INC., Westborough, MA (US)

(72) Inventors: Kester Julian Batchelor, Mound, MN (US); Thomas Faehsing, Berlin (DE); Jens M. Krueger, Zeuthen (DE); Frank Breitsprecher, Berlin (DE); Theodore C. Blus, Arden Hills, MN (US); Jordan R. Golomb, Maple Grove, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

(21) Appl. No.: 18/842,745

(22) PCT Filed: Mar. 1, 2023

(86) PCT No.: PCT/US2023/063470
§ 371 (c)(1),
(2) Date: Aug. 29, 2024

(87) PCT Pub. No.: WO2023/168260
PCT Pub. Date: Sep. 7, 2023

(65) Prior Publication Data
US 2025/0107839 A1 Apr. 3, 2025

Related U.S. Application Data

(60) Provisional application No. 63/268,724, filed on Mar. 1, 2022.

(51) Int. Cl.
*A61B 18/14* (2006.01)
*A61B 18/12* (2006.01)
(Continued)

(52) U.S. Cl.
CPC ...... *A61B 18/1445* (2013.01); *A61B 18/1233* (2013.01); *A61B 34/30* (2016.02); *A61B 2018/00607* (2013.01)

(58) Field of Classification Search
CPC . A61B 18/1445; A61B 18/1233; A61B 34/30; A61B 2018/00607
(Continued)

(56) References Cited

U.S. PATENT DOCUMENTS 6,042,580 A * 3/2000 Simpson ............ A61B 18/1492
606/41
7,931,649 B2 * 4/2011 Couture ............. A61B 18/1445
606/45
(Continued)

FOREIGN PATENT DOCUMENTS

CN 119212638 A 12/2024
JP 2000005191 1/2000
(Continued)

OTHER PUBLICATIONS

"International Application Serial No. PCT/US2023/063470, International Search Report mailed Sep. 27, 2023", 5 pgs.
(Continued)

*Primary Examiner* — Michael F Peffley
(74) *Attorney, Agent, or Firm* — Schwegman Lundberg & Woessner, P.A.

(57) ABSTRACT

A surgical system for treating tissue, the system comprising a surgical device and a control system. The surgical device can include an end effector and a sensor. The end effector can include an active electrode for treating tissue. The sensor can be configured to generate a data signal corresponding to a characteristic of the end effector or the tissue. The control system can be operably coupled to the sensor. The control system can be configured to deliver power to the active
(Continued)

electrode and can be configured to adjust the power during a period of time that the data signal is received by the control system.

20 Claims, 19 Drawing Sheets

(51) Int. Cl.
    *A61B 34/30*     (2016.01)
    *A61B 18/00*     (2006.01)
(58) Field of Classification Search
    USPC ........................................................ 606/45
    See application file for complete search history.

(56)                  References Cited

U.S. PATENT DOCUMENTS

| | | | | |
|---|---|---|---|---|
| 10,130,412 | B2 * | 11/2018 | Wham | ............... A61B 18/1445 |
| 10,695,125 | B2 * | 6/2020 | Prutchi | ............. A61B 18/1492 |
| 2006/0271035 | A1 | 11/2006 | Wheeler et al. | |
| 2011/0028963 | A1 | 2/2011 | Gilbert | |
| 2011/0087212 | A1 | 4/2011 | Aldridge et al. | |
| 2011/0270242 | A1 | 11/2011 | Marion | |
| 2014/0330266 | A1 | 11/2014 | Thompson et al. | |
| 2015/0088124 | A1 | 3/2015 | Wham | |
| 2016/0220302 | A1 | 8/2016 | Zarins et al. | |
| 2017/0238991 | A1 | 8/2017 | Worrell et al. | |
| 2021/0015550 | A1 | 1/2021 | Highsmith et al. | |
| 2021/0196363 | A1 | 7/2021 | Shelton, IV et al. | |
| 2022/0168039 | A1 | 6/2022 | Worrell et al. | |
| 2023/0255677 | A1 * | 8/2023 | Norton | ................... A61B 18/14 |
| | | | | 606/45 |

FOREIGN PATENT DOCUMENTS

| | | | |
|---|---|---|---|
| JP | | 2015066437 | 4/2015 |
| WO | WO-2023168260 | A2 | 9/2023 |
| WO | WO-2023168260 | A3 | 9/2023 |

OTHER PUBLICATIONS

"International Application Serial No. PCT/US2023/063470, Invitation to Pay Additional Fees mailed Jul. 7, 2023", 12 pgs.

"International Application Serial No. PCT/US2023/063470, Written Opinion mailed Sep. 27, 2023", 13 pgs.

"U.S. Appl. No. 18/842,745, Restriction Requirement mailed Feb. 13, 2025", 6 pgs.

"European Application Serial No. 23716088.2, Response filed Apr. 7, 2025 to Communication pursuant to Rules 161(1) and 162 EP", w/ claims, 9 pgs.

"International Application Serial No. PCT/US2023/063470, International Preliminary Report on Patentability mailed Sep. 12, 2024", 15 pgs.

"Japanese Application Serial No. 2024-552042 Voluntary Amendment Filed Oct. 30, 2024", w/ english claims, 5 pgs.

"Japanese Application Serial No. 2024-552042, Notification of Reasons for Refusal mailed Aug. 26, 2025", w English Translation, 11 pgs.

\* cited by examiner

Proximal

1504

1510
1514
1516
1518

1502

1500

1520

1512

1506

Distal

1508

A1

1526

1562

FEEDBACK CONTROL IN ELECTROSURGICAL SYSTEMS

CLAIM OF PRIORITY

This patent application is a U.S. National Stage filing under 37 U.S.C. § 371 from International Application No. PCT/US2023/063470, entitled "FEEDBACK CONTROL IN ELECTROSURGICAL SYSTEMS," filed on Mar. 1, 2023, which claims the benefit of priority, under 35 U.S.C. Section 119(e), to U.S. Patent Application Ser. No. 63/268, 724, entitled "THERMAL FEEDBACK CONTROL," filed on Mar. 1, 2022, the contents of which are hereby incorporated by reference herein in their entireties.

BACKGROUND

Tissue or organs of the human body often require surgical intervention which can include removal of tissue, organs, or portions thereof. In some cases, organs or tissue can be removed for sample collection, such as for a biopsy, in other examples, organs or tissue can be removed to address one or more problems or symptoms experienced by a patient. In either case, specialized surgical instruments can be used to safely and efficiently remove the organs or tissue.

Electrosurgery is the application of electrical energy to produce a change in biological tissue of a surgical patient in some manner. Various electrosurgical techniques can be used to cut, coagulate, desiccate, or fulgurate the biological tissue. These electrosurgical techniques and others can be performed during various medical procedures, such as, for example, laparoscopic surgeries. Examples of these medical procedures can include: appendectomy, cholecystectomy, colectomy, cystectomy, gastric banding, gastric bypass, hernia repair, nephrectomy, Nissen fundoplication, prostatectomy, sleeve gastrectomy, or others. Each of these medical procedures can have one or more electrotherapeutic phases, such as, for example, an interrogation phase, a heating phase, a drying phase, a cauterizing phase, or the like.

Electrosurgical devices can use alternating current (AC) electrical energy such as at an energy level and frequency appropriate to cut or coagulate tissue. The use of alternating current requires that the circuit be closed. Electrosurgical devices can be monopolar (e.g., devices or systems that use a relatively more distant electrode, such as a dispersive electrode pad, to close the circuit) or bipolar (e.g., devices that use one or more electrodes in close proximity such as can be located on the end of a handpiece of the device to close the circuit). In monopolar devices, an electrical therapy signal generator can provide current that travels from the electrode in the handpiece through the body to a dispersive pad, to return current back to the generator. In bipolar devices, such as electrosurgical forceps, the current from the generator can travel down one leg of the forceps and, via tissue, over to another other leg of the forceps, from where the current can return to the generator.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
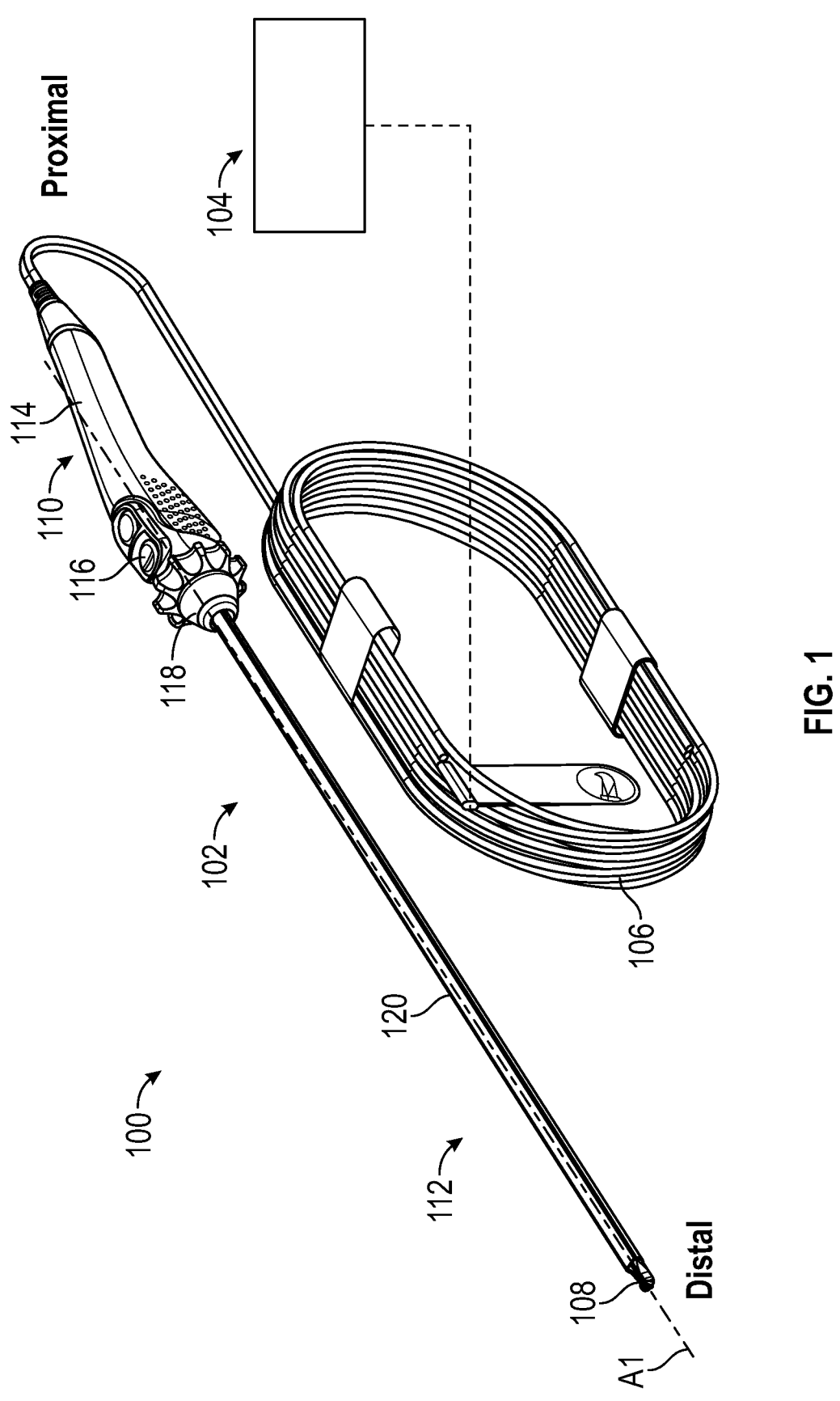
FIG. 1 illustrates an isometric view of a surgical system.

Various surgical devices can receive electrical energy (or radiofrequncy (RF) energy or ultra-high frequency (UHF) energy). For example, electrosurgical devices can use electrodes to perform partial or completely hemostatic cuts or resections of the tissue using electrical energy (RF energy or UHF energy) delivered to the tissue through an active electrode of a bipolar or monopolar device. Use of monopolar systems can result in large thermal margins, which, in turn, can later result in tissue necrosis after cutting. Necrosis can be especially problematic if the electrosurgical tissue treatment is intended to seal a resected wound area to promote healing. Further, monopolar outputs can affect nearby nerve tissue. Nerve tissue, once past the outer mylar sheath of the nerve, is significantly more electrically conductive than the surrounding tissue. Therefore, a nerve can provide a preferred path along which electrosurgical treatment current passes. Unintended electrical conduction of electrosurgical energy along a nerve can affect suture integrity, can cause denervation, and can cause other unintended results.

An electrosurgical end effector can also experience thermal runaway, which can occur when heat generated by the electrosurgical end effector exceeds the amount of heat dissipated to the surroundings. Thermal runaway can be associated with reduction in volumetric resistivity as the temperature of the tip (and its surroundings) increase. Some materials can help reduce thermal runaway (e.g., high-temperature, low thermal conductivity materials). However, material choice alone may not prevent thermal runaway and subsequent issues. Thermal runaway can cause a continuous arc to be formed between the two electrode poles of a bipolar device rather than between the tissue and the electrode. This arc can remain in a particular location, once established, creating a highly energized area that, due to its lower volumetric resistivity and charged ionization pathway, can persist in the same general location eventually bridging (and melting) the insulator. These concerns may be especially prevalent when a novice user of a monopolar electrical system simply uses a convenient default power setting as opposed to an optimal power setting appropriate for performing the desired electrosurgical procedure.

To help overcome one or more of the issues associated with monopolar electrosurgical treatment systems, bipolar electrosurgical treatment devices can be used such as for performing cutting or other electrosurgical treatment. In a bipolar device, a passive electrode can receive the electrical energy from the tissue, allowing energy to flow through the tissue to perform the cut or resection. The electrodes can be separated by one or more dielectric components to help ensure energy flows through the tissue. An electrosurgical device with a bipolar electrosurgical end effector, such as a J-Hook, can provide a controlled tissue cutter that need not send as high voltage energy through the patient to a remote return electrode pad, such as is the case when using a monopolar electrosurgical device. Also, because a bipolar electrosurgical device can provide its electrosurgical energy more locally and at a lower voltage, thermal margins can be lower. Therefore, a bipolar electrosurgical device can help promote better healing of treated or affected tissue as compared to a monopolar (or diathermy) cutting modality.

Some electrosurgical end effectors, such as J-Hooks, can be part of a "plug and play" system that can provide controlled energy output platform. The bipolar electrosurgical energy delivered by the end effector can be limited and controlled such as to establish, adjust, or otherwise provide the appropriate power, as opposed to providing a fixed power output, which may be more difficult for certain applications or for certain users. However, such bipolar electrosurgical devices may still need large thermal dissipation capability because electrodes can heat up significantly during cutting or resection due to flowing energy and due to contact between the electrodes and relatively hot tissues. Both the device temperature and the applied electrosurgical power can affect device function and therapy results. Excessive heating of the electrodes during use can cause overheating, which can lead to dielectric breakdown, dielectric melting, tissue necrosis, or other issues. Currently, devices such as the J-Hook™ cutting and coagulation device, use long electrode return arms to address these issues. The return electrode arms extend through the shaft and connect to a handpiece of the instrument. The return arms can serve as heat sinks to aid in cooling the cutting tip to help reduce overheating of the electrodes. To help achieve better thermal control, the device working tip can include large heat sinks for transferring heat away from the return electrodes, such as to allow for worst case conditions and use-cases for the electrosurgical activation. Such instruments can include tips that are relatively large, which can affect surgical precision. Also, though effective, the return heat sinks can be made of highly conductive materials, such as copper, which can be relatively expensive to manufacture and assemble.

The present disclosure can help to address these issues by including relatively smaller heat sinks, and by managing overheating by controlling power delivery via the active electrode, such as to limit to a voltage or current delivered to and by the end effector. In an example, temperature at a working tip of the electrosurgical instrument device can be monitored. As the temperature at the device tip increases, an arcing voltage across the gas gap decreases. By lowering a maximum allowable output voltage between the electrodes as the local temperature increases, direct arcing and thermal runaway can be reduced. A small, evenly distributed, ionized pocket of arcing along the intended blade length can be obtained, thereby enabling predictable RF cutting or other treatment to be achieved.

Through a sensor in a tip of the end effector, the present system can include feedback control, such as to sense a temperature of a heatsink (or other component) of the surgical instrument and. In response, a controller circuit can control the electrosurgical energy generator, such as to adjust the power that is being delivered to the electrosurgical instrument device. Such local temperature sensing, e.g., via the heatsink, and responsive voltage or power control of the electrosurgical energy being delivered by the electrosurgical energy treatment device can allow the device to include relatively smaller heatsinks while still remaining safe and efficient and reducing the risk of thermal runaway.

The above discussion is intended to provide an overview of subject matter of the present patent application. It is not intended to provide an exclusive or exhaustive explanation of the invention. The description below is included to provide further information about the present patent application.

FIG. 1 illustrates an isometric view of a surgical system 100. The surgical system 100 can include a surgical instrument 102 that can be connected to a generator 104, such as via one or more wires or conductors 106. The generator 104 can be an electrical or electromagnetic device configured to deliver energy to the handpiece 110. The generator 104 can include one or more controller or control circuits, such as one or more components of the devices and systems of FIGS. 20 and 21. The surgical instrument 102 can include an end effector 108, a handpiece 110, and an intermediate portion 112. The handpiece 110 can include a housing 114, controls 116, and a rotational actuator 118. FIG. 1 also shows orientation indicators Proximal and Distal and a longitudinal axis A1.

Generally, the handpiece 110 can be located at a proximal end of the instrument 102 and the end effector 108 can be located at a distal end of the surgical instrument 102. The intermediate portion 112 can extend between the handpiece 110 and the end effector 108 to operably couple the handpiece 110 to the end effector 108. Various movements of the end effector 108 can be controlled by one or more actuation systems of the handpiece 110. For example, the end effector 108 can be rotated along the longitudinal axis A1 of the surgical instrument 102. The handpiece 110 can also be used to operate the end effector 108 for cutting tissue, such as via delivery of electric or electromagnetic energy to tissue.

The housing 114 can be a frame that provides structural support between components of the surgical instrument 102. The housing 114 is shown as housing at least a portion of the actuation systems associated with the handpiece 110 for operating the end effector 108. However, some or all of the components need not be housed within the housing 114. The housing 114 can provide a rigid or semi-rigid structure for attachment of components, but the housing 114 does not necessarily house the components completely, or can house a portion of one or more of the components.

The intermediate portion 112 can include a shaft 120 that can extend between the housing 114 and the end effector 108 and can be configured to support one or more components therein. The controls 116 can be coupled to the housing 114 and can include or be connected to electronic circuitry within the housing 114, such as to connect the controls 116 to the generator 104. Such circuitry can send or transmit electric or electromagnetic energy to the end effector 108. In some examples, the electronic circuitry may reside outside the housing 114 but can be operably coupled to the housing 114 and the end effector 108.

In operation of some examples, a user can use the rotational actuator 118 to orient or rotate the end effector 108 as desired, such as to contact tissue of a patient. When it is desired to resect or cut the tissue, the user can operate the controls 116 to cause an electromagnetic energy, electric energy, RF energy, or UHF energy, to be delivered to the end effector 108, such as to an electrode thereof, and to the tissue. Application of such energy can be used to cut and seal (e.g., hemostatically cut) or otherwise affect the tissue engaged with the end effector 108. Throughout use of the end effector 108 for such actions, the rotational actuator 118 can be operated to orient the end effector 108 as desired. Such a process can be repeated as desired or necessary to resect or treat an affected area. Though the end effector 108 is discussed above as being an electrosurgical cutting instrument, the end effector 108 can be various other tools, as discussed below.

Figure 2:
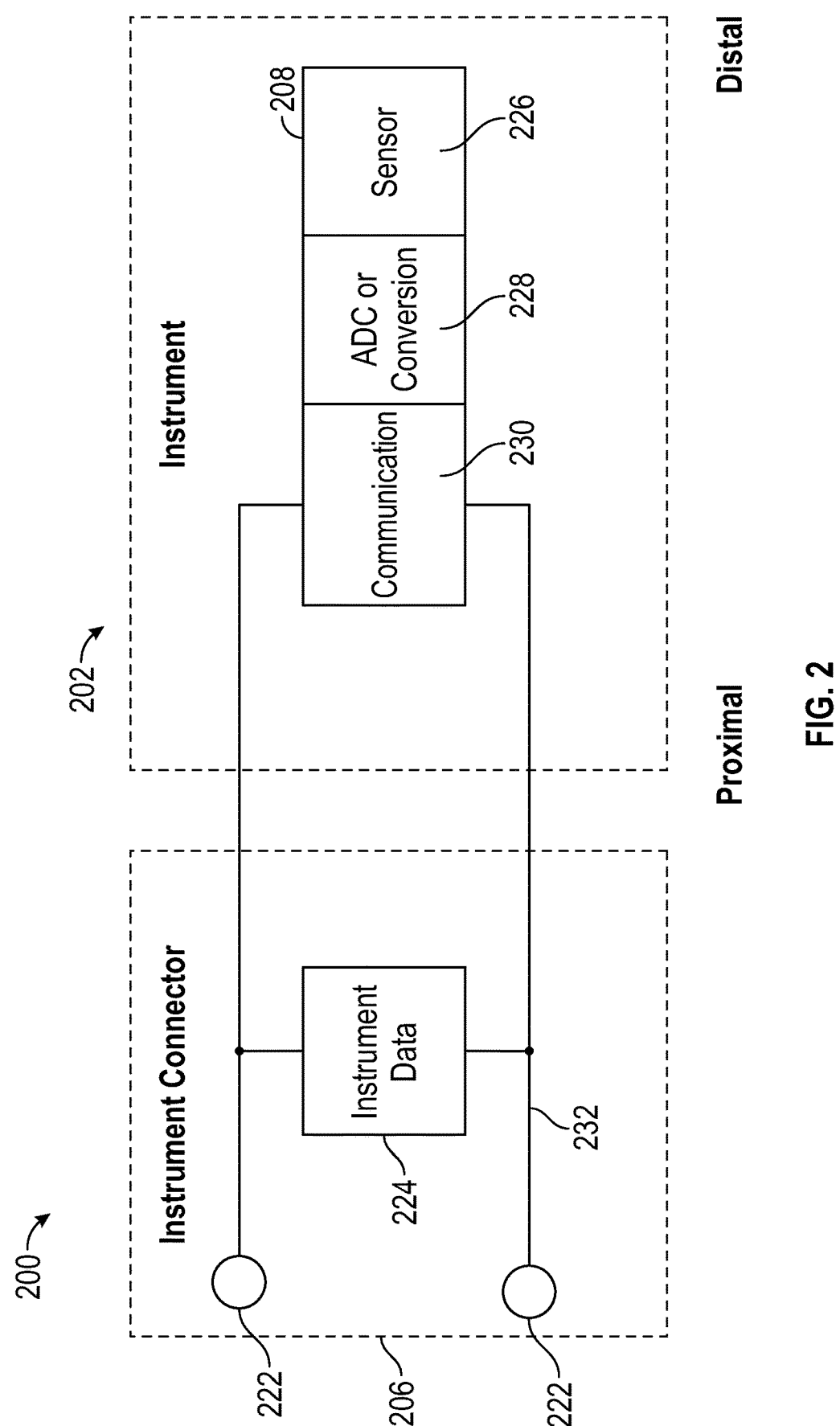
FIG. 2 illustrates a schematic view of a portion of a surgical system.

FIG. 2 illustrates a schematic view of a portion of a surgical system 200. The surgical system 200 can be similar to the surgical system 100 discussed above. FIG. 2 shows a schematic view of how such a system can be configured. Any of the systems discussed above or below can be modified to include the features of the surgical system 200. FIG. 2 also shows orientation indicators Proximal and Distal.

The surgical system 200 can include a surgical instrument 202 and conductors or connectors 206. The surgical instrument 202 can include an end effector 208. The conductors 206 can be connected to a generator (e.g., the generator 104) such as via terminals or contacts 222. The connectors 206 can also include memory 224. The memory 224 can be various types of memory, such as semiconductor memory devices (e.g., Electrically Programmable Read-Only Memory (EPROM), Electrically Erasable Programmable Read-Only Memory (EEPROM)), flash memory devices, magnetic disks, or the like.

The surgical instrument 202 can also include a sensor 226, a converter 228, and a transceiver (or transmitter) 230. The memory 224, the sensor 226, the converter 228, and the transceiver 230 can be connected by, or part of, a circuit 232. The sensor 226 can be a temperature sensor, a force sensor, a pressure sensor, an angle sensor, a proximity sensor, a distance sensor, an amount of tissue sensor, a contact sensor, an optical sensor, an infrared sensor, an ultrasonic sensor, a particulate sensor, or the like. The sensor 226 can be configured to produce a data signal indicative of a condition of the surgical instrument 202 (e.g., the end effector 208) or a condition of tissue engaged with or nearby the end effector 208 (or the sensor 226). The end effector 208 can be a hook-shaped device, a spatula, a forceps, an electrode, an electrosurgical pencil, a monopolar electrosurgical cutting instrument, a bipolar electrosurgical cutting instrument, a coagulator, an irrigator, or the like.

The converter 228 can be connected to the sensor 226 and the transceiver 230. The converter 228 can be an analog to digital converter (ADC) or other converter, circuit, or chip configured to convert or otherwise process the data signal from the sensor 226. The transceiver 230 can be a transmitter or transceiver configured to transmit the converted signal from the surgical instrument 202 to the memory 224. The surgical system 200 can be used to perform one or more procedures, as discussed in further detail below.

Figure 3:
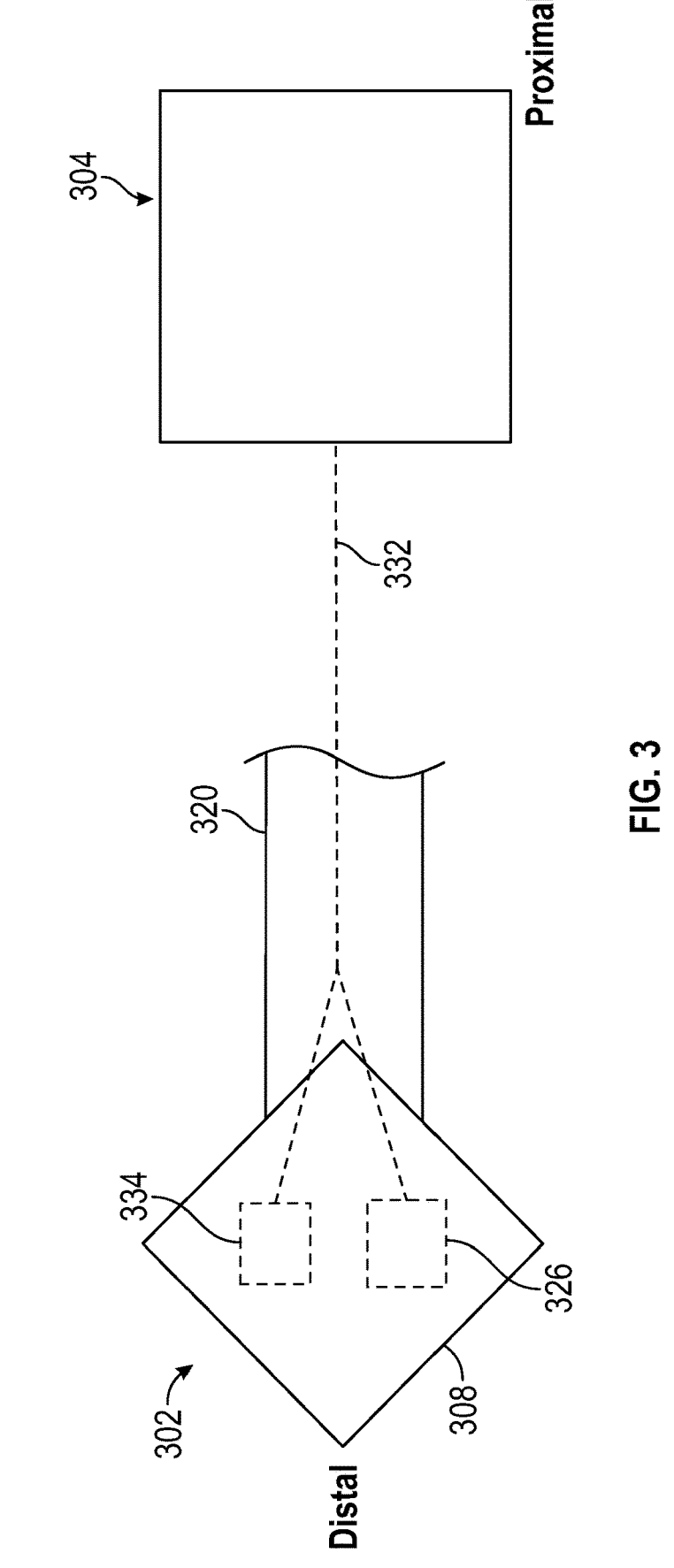
FIG. 3 illustrates a schematic view of a portion of a surgical system.

FIG. 3 illustrates a schematic view of a portion of a surgical system 300, which can be similar to the surgical system 100 or the surgical system 200 discussed above. FIG. 3 shows, schematically, how the surgical system 300 can be arranged. Any of the systems discussed above or below can be modified to include the features of the surgical system 300. Operation of the surgical system 300 is also discussed below.

The surgical system 300 can include a generator 304, which can be similar to the generator 104 discussed above. The surgical system 300 can also include a surgical instrument 302, which can be similar to the surgical instrument 102 or the surgical instrument 202 discussed above. The surgical instrument 302 can also include a shaft 320 connected to an end effector 308 at a distal end of the shaft 320. The end effector 308 can include a sensor 326 (which can be similar to the sensor 226) and an active electrode 334 that can be connected to the generator 304, such as via a circuit 332. The circuit 332 can optionally be at least a portion of a one-wire EEPROM circuit (or 1-wire EEPROM communication bus). The circuit 332 can be driven from a single digital input/output (I/O) terminal or contact on a controller of the generator 304 and the circuit 332 can be connected to a ground pin or terminal. The circuit 332 is discussed as being a 1-wire EEPROM circuit, but can be other types of 1-wire communication bus circuits in other examples.

In operation of some examples, the surgical instrument 302 can be used during one or more procedures where tissue is engaged or observed. In such a procedure, the surgical instrument 302 can be manipulated such that the end effector 308 engages or interacts with tissue (or is positioned near tissue). The generator (e.g., the generator 104) can deliver power to the active electrode 334 of the end effector 308 to affect tissue. The control system or generator can then reduce the power delivered to the active electrode 334 of the end effector 308, such as to help reduce interference from the power delivered to the active electrode 334. Optionally, the RF or HF energy can be modified or reduced to a level that causes less interference and not stopped or interrupted altogether. The generator 304 can then receive, from the sensor 326 when the power delivered to the end effector is reduced, the data signal from the 326, which can be indicative of at least one characteristic of the end effector 308 or the tissue.

The generator 304 can use the data signal from the sensor 326 to determine one or more characteristic of the tissue or the end effector 308. In an example where the sensor 326 is a temperature sensor, the generator 304 can use the data signal to determine a temperature of at least a portion of the end effector 308. The generator 304 can then adjust the power delivered to the active electrode 334 based on the determined temperature.

That is, the generator 304 can determine the characteristic representative of a component, such as a temperature of a return electrode, based on the data signal generated by the sensor 326 during a period of time when the power delivered to the active electrode 334 of the end effector 308 is reduced. Optionally, the power can be reduced by the generator 304 for a relatively short duration, such as to help limit impact of operation of the surgical instrument 302. For example, the generator 304 can reduce the power delivered to the end effector 308 for a duration or interval between 10 milliseconds and 100 milliseconds during an instance of measuring the data signal. In another example, the generator 304 can reduce the power delivered to the end effector 308 for a duration between 10 milliseconds and 50 milliseconds during an instance of measuring the data signal. In another example, the generator 304 can reduce the power delivered to the end effector 308 for a duration between 20 milliseconds and 80 milliseconds during an instance of measuring the data signal. In another example, the generator 304 can reduce the power delivered to the end effector 308 for a duration between 30 milliseconds and 50 milliseconds during an instance of measuring the data signal. The generator 304 can reduce the power by reducing one or more of the voltage, current, or the like.

Because the active electrode 334 and the sensor 326 share a conductor (e.g., the circuit 332), such as of a one-wire EEPROM circuit, reduction of power to the active electrode 334 can allow the generator 304 to receive the data signal from the sensor 326 with reduced noise or interference, allowing the generator 304 to use the data signal to more accurately determine one or more or characteristic of the end effector 308 or the tissue. The generator 304 can then use the determined characteristic to adjust operation of the surgical instrument 302. For example, based on the determined characteristic, the generator 304 can automatically adjust a power delivered to the active electrode 334, such as to help limit overheating of the end effector 308 or one or more components thereof.

The surgical system 300 can also include a dynamic or other feedback control loop to adjust (e.g., automatically) the power or voltage that is being delivered to the device. The control loop can include a voltage limit, a power limit, a current limit, or the like. The limit or an operating parameter of the surgical instrument 302 can be modified (e.g., by the generator 304) such as based on the sensed temperature of the end effector 308 (or a component thereof), such as to limit or otherwise control delivery of the electrosurgical energy or power such that direct arcing and localized thermal runaway is limited or prevented.

In an example, an end effector 308 temperature can be monitored by the generator 304 in a number of ways, including performing temperature sensing directly on or within a heatsink itself. In an example, a temperature sensor or thermocouple can provide temperature feedback from the end effector 308 or an associated heatsink and can allow a modulated output electrosurgical energy parameter to be established or adjusted in a manner such as to inhibit or prevent undesired arcing, undesired thermal runaway, or both.

Optionally, operation of the surgical system 300 or the generator 304 to determine a characteristic of the end effector 308 can includes several iterations or steps. For example, the generator 304 can provide or deliver energy to the active electrode 334 and then interrupt or reduce power or energy delivered to the active electrode 334. With power reduced, the generator 304 can receive the data signal from the sensor 326 and determine a characteristic of the end effector 308 (such as a temperature of the return electrode). The generator 304 can then deliver energy again to the active electrode 334, such as at a modified power or energy, and can then interrupt or reduce power again to receive or analyze the data signal before power is restored again, optionally at a different power or energy level that can be the same or different from any of the previously delivered power or energy levels.

Optionally, repetition of sensing or determining a characteristic (e.g., performed by the generator 304) can include switching energy output of the generator 304 to the active electrode 334 between cutting energy, coagulating energy, and an energy or power level for receiving the signal or analyzing the signal to determine one or more characteristic. Optionally, multiple instances of cutting and coagulating can be performed before each instance of receiving the signal or analyzing the signal. Optionally, receiving the signal or analyzing the signal can be performed between each instance of cutting or coagulating.

Optionally, the generator 304 can determine a rate of change of a characteristic, such as over time, or between measurements. Such a rate of change can be used to control power delivered to the end effector 308. For example, the generator 304 can use the sensor 326 to determine a rate of change of temperature over time using multiple measurements. As the temperature rate of change increases, the generator 304 can reduce a maximum available power to help reduce overheating or other issues.

Optionally, the generator 304 can determine a difference between a characteristic rate of change at a first time and a characteristic rate of change at a second time, to help determine a characteristic acceleration. For example, a temperature rate of change at a first time and a temperature rate of change at a second time can be determined by the generator 304 based on a signal from the sensor 326. When the generator 304 determines that the temperature is increasing quickly (such as beyond a temperature acceleration threshold), energy or power delivered to the end effector 308 can be decreased. Such analysis can help to provide an earlier prediction that an issue may occur.

In some examples, multiple characteristic thresholds can be used. For example, the generator 304 can use a first characteristic threshold, where, when passed, the generator 304 can reduce power below a first limit, and the generator 304 can use a second characteristic threshold, where, when passed, the generator 304 can reduce power below a second limit, which can be different (i.e., higher or lower) than the first limit.

In some examples, one or more characteristic threshold types can be considered together in determining an energy output, such as a characteristic value and a rate of change of the characteristic. For example, both a determined temperature can be considered as well as a rate of change of temperature where each can be compared to a different threshold, or both can be combined and compared to a combination threshold to make one or more determinations on power delivered to the end effector 308 by the generator 304.

In another example, thermal monitoring can be performed when the sensor 326 is an infrared or other optical sensor. Optionally, imaging or other visualization system that can be part of the device or system itself or a standalone system can be used. In an example, a standalone thermal monitoring system can be mounted on or other located at or near the electrosurgical device, as discussed below with regard to FIG. 15. Further examples of devices and methods using these various techniques are discussed below.

Figure 4:
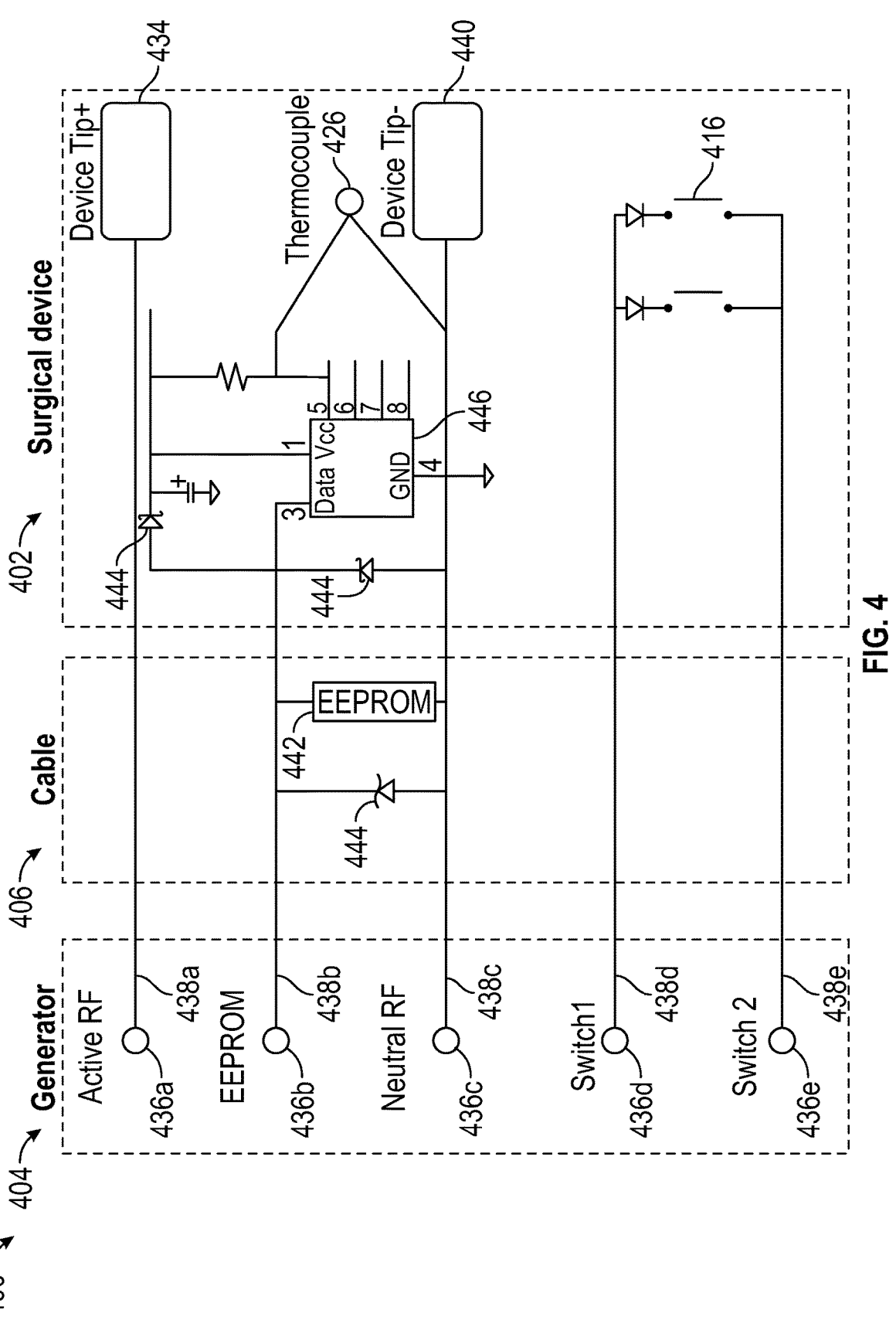
FIG. 4 illustrates a schematic view of a portion of a surgical system.

FIG. 4 illustrates a schematic view of a portion of a surgical system 400. The surgical system 400 can be similar to any of the surgical systems discussed above. FIG. 4 shows an electrical or control schematic of the surgical system 400. Any of the systems discussed above or below can be modified to include the features of the surgical system 400.

The surgical system 400 can include a surgical instrument 402, which can be similar to the surgical instrument 102 (or the surgical instrument 202 or the surgical instrument 302). The surgical system 400 can also include a cable 406, which can be similar to the conductors 106. The surgical system 400 can also include a generator 404, which can be similar to the generator 104 (or the generator 304). The generator 404 can include terminals 436a-436e to which conductors 438a-438 can be connected, respectively. The terminals 436 can be contacts, terminals, or other electrical connections configured to electrically (or otherwise connect) components to the generator 404. The conductors 438 can be wires, traces, conductors, optical fibers, or the like and can be configured to transmit energy (e.g., electrical or optical) between connected components, such as a component of the surgical instrument 402 and the generator 404.

The surgical instrument 402 can include an end effector 408 that can include a sensor 426, an active electrode 434, and a return electrode 440. The surgical instrument 402 can also include one or more controls 416 (which can be similar to the controls 116). The active electrode 434 can be connected to the terminal 436a by the conductor 438a. The return electrode 440 can be connected to the terminal 436c by the conductor 438c such that power delivered by the terminal 436a can flow from the active electrode 434 to tissue and to the terminal 436c via the return electrode 440 and the conductor 438c.

The controls 416 can be connected to the terminals 436d and 436e by conductors 438d and 438e, respectively. The sensor 426 and the return electrode 440 can be connected to the terminals 436b and 436c by conductors 438b and 438c, respectively, which can include or can be part of a one-wire EEPROM circuit, including an EEPROM device 442, diodes 444, and an ADC 446. The ADC 446 can be or can include one or more chips or boards configured to receive an analog signal and produce or generate a digital signal based on the analog signal. For example, the ADC 446 can generate a digital signal based on a data signal produced by the sensor 426.

To help reduce a number of terminals required to incorporate the sensor 426, the return electrode 440 can share the conductor 438c with the one-wire EEPROM circuit. As discussed above, the sensor 426 can be used by the generator 404 to help ensure the surgical instrument 402 is operating correctly and within desirable operating conditions. For example, the sensor 426 can be a temperature sensor configured to produce a temperature signal based on a temperature of the return electrode 440. The generator 404 can use the temperature signal to determine a temperature of the return electrode 440, and the generator 404 can reduce power to the active electrode 434 when a temperature of the sensor 426 surpasses or approaches a threshold temperature, such as to help reduce overheating (or other issues) of the return electrode 440 or the dielectric.

However, due to sharing the conductor 438c, when the active electrode 434 receives power from the generator 404 and the return electrode 440 receives power from the tissue, the data signal from the sensor 426 can be difficult for the generator 404 to process or interpret due to noise or interference from the received power. To help address this issue, power delivered to the active electrode 434 from the generator 404 can be reduced during a period or interval. The interval or period of reduced power can be an amount of time where power delivered by the generator 404 is reduced from its previous amount, such as by reducing current, voltage, or the like. During the reduced or interrupted power interval, the ADC 446 can receive the data signal from the sensor 426 and can transmit a digital signal, which can optionally be stored in the EEPROM device 442 and can be read by the generator 404 (such as by a controller thereof).

Reduction of power by the generator 404 to the active electrode 434 for determination of the characteristic or reception or analysis of the data signal can be a reduction in voltage, current, or the like for a period of time, such that RF energy or UHF energy (and power) is reduced. The reduction or adjustment can be reduced to a power or energy level where radiofrequency interference is reduced to a level that permits sensor data from the sensor 426 to be transmitted from the sensor 426 to the generator 404 without excessive interference that would render the sensor data unusable (or less usable) for its intended purpose, or would require additional processing by the generator 404 to read or use data from the data signal of the sensor 426.

Once the reading is performed or the data signal is processed or analyzed, the characteristic of the sensor 426 or the tissue can be determined. Once the characteristic is determined, power can be reenabled and can be reduced when the characteristic is determined to be beyond a threshold. The characteristic can be determined after power is reduced or interrupted and before, during, or after the power is restored. Such a process can be repeated in intervals, such as once per second, once per 5 seconds, once per 10 seconds, once per minute, once per power activation, or the like. Using this process, the generator 404 can determine a characteristic of the surgical instrument 402 or the tissue using the sensor 426 that shares a conductor with the return electrode 440.

Figure 5:
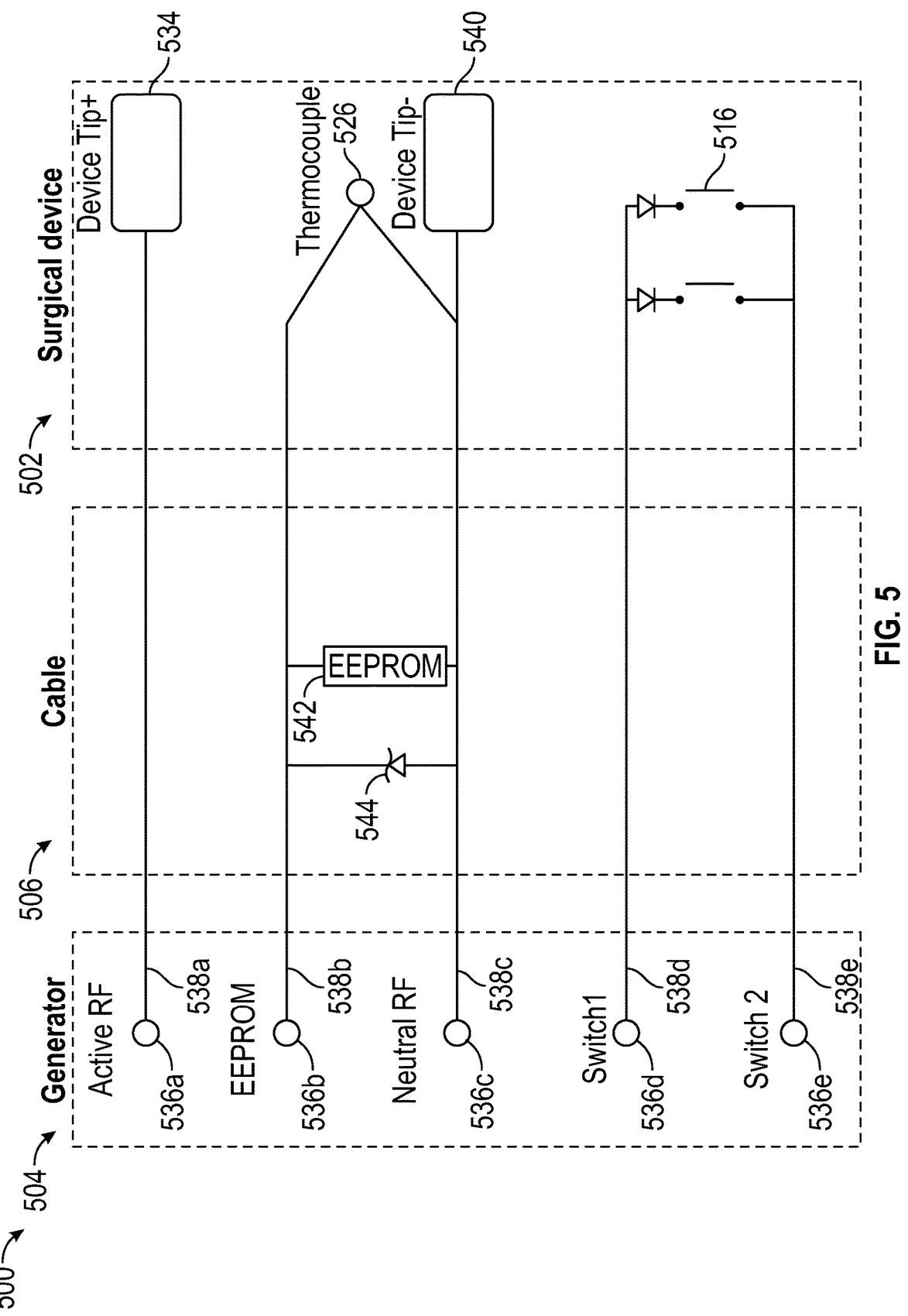
FIG. 5 illustrates a schematic view of a portion of a surgical system.

FIG. 5 illustrates a schematic view of a portion of a surgical system 500. The surgical system 500 can be similar to the surgical system 400 discussed above; the surgical system 500 can include a circuit produces an analog signal. Any of the systems discussed above or below can be modified to include the features of the surgical system 500.

The surgical system 500 can be connected similarly to the surgical system 400 discussed above without an ADC. That is, a sensor 526 and a return electrode 540 can be connected to terminals 536b and 536c by conductors 538b and 538c, respectively, which can include or can be part of a one-wire EEPROM circuit, including an EEPROM device 542, and a diode 544. An active electrode 534 can be connected to a terminal 536a by a conductor 538a. And, controls 516 can be connected to terminals 536d and 536e by conducts 538d and 538e, respectively.

The return electrode 540 can share the conductor 538c with a one-wire EEPROM circuit, helping to reduce a number of terminals required to incorporate the sensor 526. The sensor 526 can be used by the generator 504 to help ensure the surgical instrument 502 is operating correctly and within desirable operating conditions. For example, the sensor 526 can be a temperature sensor configured to produce an analog temperature signal based on a temperature of the return electrode 540. The generator 504 can use the analog temperature signal to determine a temperature of the return electrode 540, and the generator 504 can reduce power to the active electrode 534 when a temperature of the sensor 526 surpasses or approaches a threshold temperature, such as to help reduce overheating (or other issues) of the return electrode 540 or the dielectric.

Because the conductor 538c is shared, when the active electrode 534 receives power from the generator 504 and the return electrode 540 receives power from the tissue, the data signal from the sensor 526 can be difficult to read due to noise or interference from the received power. To help address this issue, power delivered to the active electrode 534 from the generator 504 can be reduced during a period or interval. During the reduced or interrupted power interval, the data signal from the sensor 526 can be stored in the EEPROM device 542 or can be read by the generator 504 (such as by a controller thereof).

Once the reading is obtained, power can be restored to its previous level by the generator 504 while the characteristic of the sensor 526 or the tissue is determined. Once the characteristic is determined, power can be maintained or can be reduced when the characteristic is determined to be beyond a threshold. Using this process, the generator 504 can determine a characteristic of the surgical instrument 502 or the tissue using an analog signal from the sensor 526.

Figure 6:
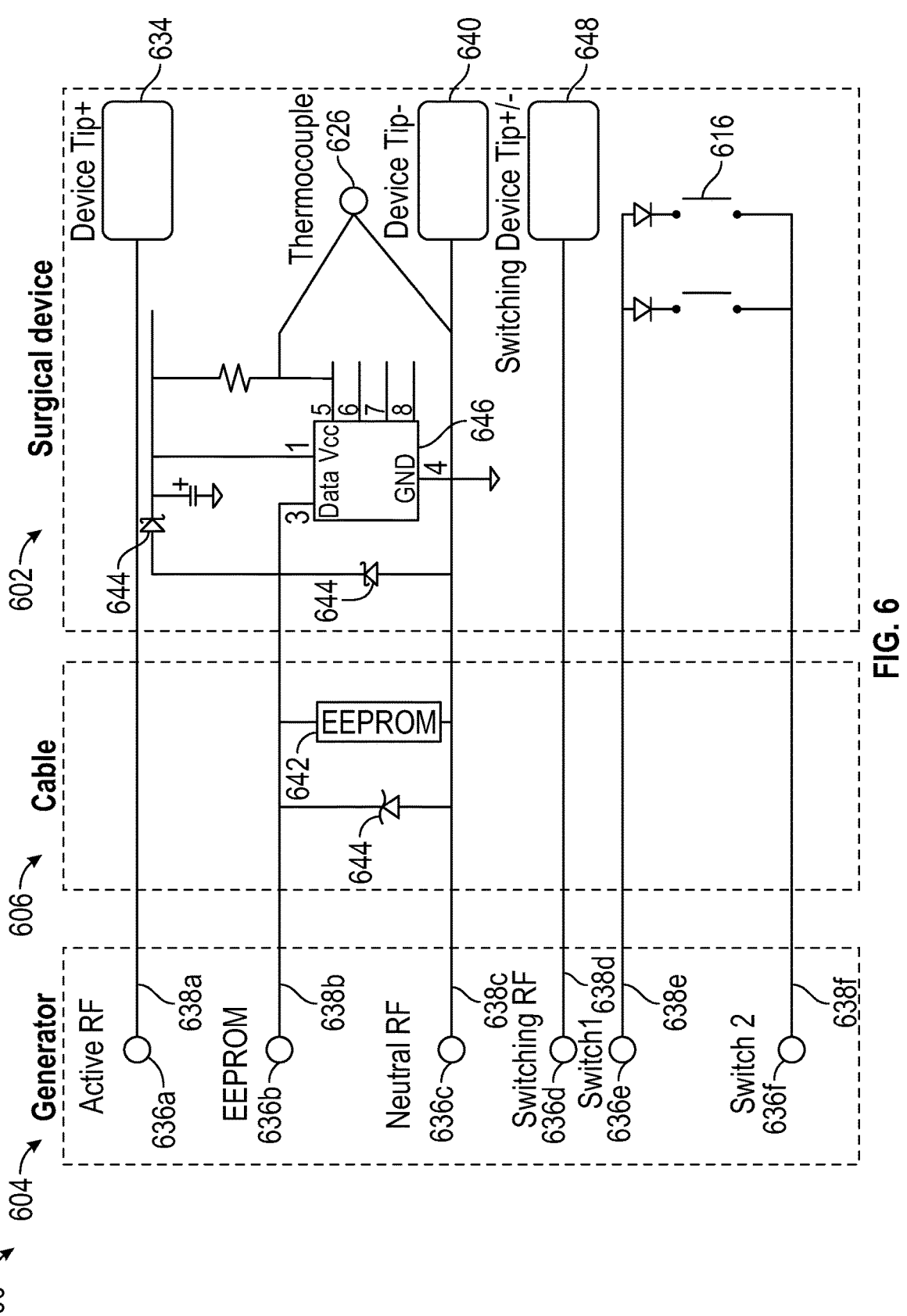
FIG. 6 illustrates a schematic view of a portion of a surgical system.

FIG. 6 illustrates a schematic view of a portion of a surgical system 600. The surgical system 600 can be similar to the surgical systems discussed above. The surgical system 600 can include a switching electrode. Any of the surgical systems discussed above or below can be modified to include the components of the surgical system 600.

The surgical system 600 can be similar to the surgical system 400 in that the surgical system 600 can include a generator 604 including contacts 636*a*-636*f*. The surgical system 600 can include a surgical instrument 602 including controls 616, a sensor 626, an active electrode 634, a return electrode 640, and a switching electrode 648. The surgical system 600 can also include a cable 606, which can include a one-wire EEPROM circuit, including an EEPROM device 642, diodes 644, and an ADC 646.

The surgical system 600 can operate similarly to the surgical system 400 and the surgical system 500 discussed above. When it is desired to obtain a reading from the sensor 626, power to the active electrode 634 or the switching electrode 648 can be reduced, adjusted, or inhibited by the generator 604 for an instance, period, or duration. During the period of reduced power, a data signal from the sensor 626 can be, the ADC 646 can receive the data signal from the sensor 626 and can transmit a digital signal, which can optionally be stored in the EEPROM device 642 and can be read by the generator 604 (such as by a controller thereof). The generator 604 can determine one or more characteristics of the sensor 626, the surgical instrument 602, or the tissue, and the generator 604 can optionally adjust power to one or more of the active electrode 634 or the switching electrode 648 based on the determined characteristic, such as if one or more thresholds for the characteristics are passed.

Figure 7:
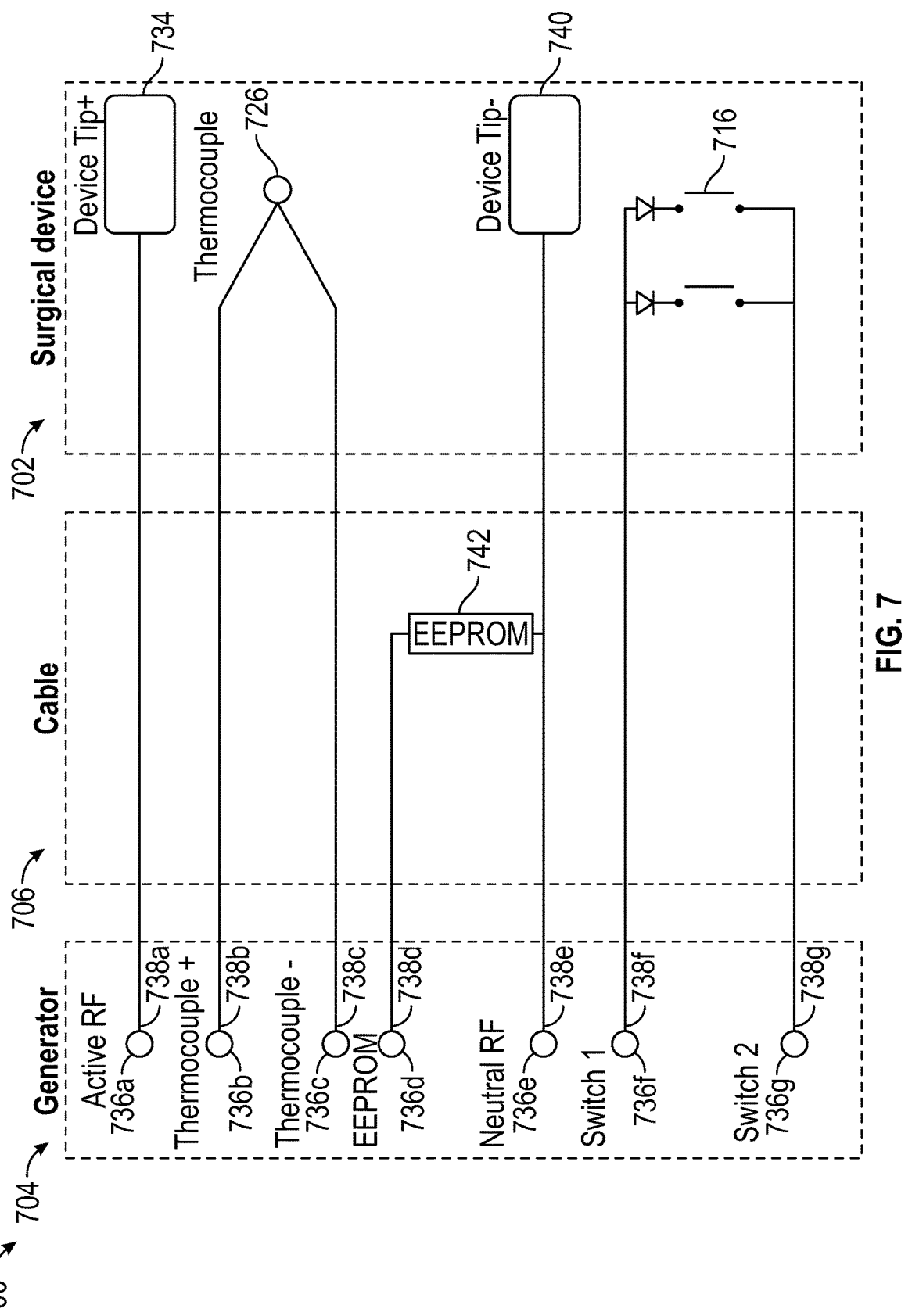
FIG. 7 illustrates a schematic view of a portion of a surgical system.

FIG. 7 illustrates a schematic view of a portion of a surgical system 700. The surgical system 700 can be similar to the surgical systems discussed above. The surgical system 700 can include a dedicated circuit for the sensor. Any of the surgical systems discussed above or below can be modified to include the components of the surgical system 700.

The surgical system 700 can be similar to the surgical system 700 in that the surgical system 700 can include a generator 704 including contacts 736*a*-736*g*. The surgical system 700 can include a surgical instrument 702 including controls 716, a sensor 726, an active electrode 734, and a return electrode 740. The surgical system 700 can also include a cable 706, which can include a one-wire EEPROM circuit, including an EEPROM device 742. The sensor 726 can be connected to terminals 736*b* and 736*c* via conductors 738*b* and 738*c*, respectively, such that the sensor 726 is independently connected to the generator 704. And, the return electrode 740 can be connected to terminals 736*d* and 736*e* via conductors 738*d* and 738*e*, respectively, such that the return electrode 740 is independently connected to the generator 704.

The surgical system 700 can operate similarly to the surgical systems 400-600 discussed above. However, when it is desired to obtain a reading from the sensor 726, because the sensor 726 is on a dedicated circuit, the power to the active electrode 734 may not be reduced, adjusted, or inhibited, due to a lack of interference on the sensor circuit. A data signal from the sensor 726 can be transmitted to the generator 704, such as via the EEPROM device 742. The generator 704 can determine one or more characteristics of the sensor 726, the surgical instrument 702, or the tissue, and the generator 704 can optionally adjust power to the active electrode 734 based on the determined characteristic, such as if the generator 704 determines that one or more thresholds for the characteristics are passed. Also, because the sensor 726 is on a dedicated circuit, a relatively smaller sensor or thermocouple can be used, further helping to reduce a size of a tip of the surgical instrument 702.

Figure 8:
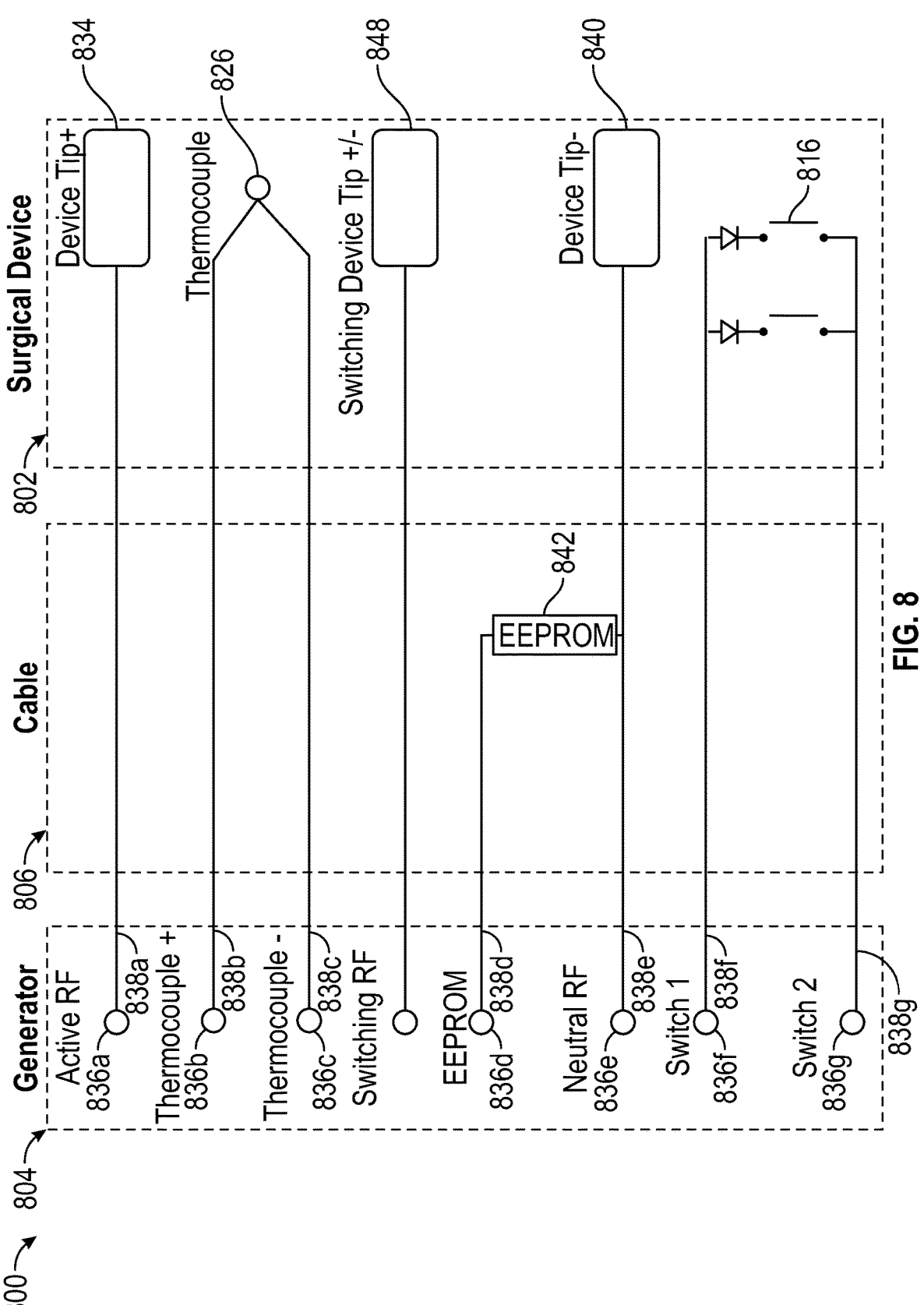
FIG. 8 illustrates a schematic view of a portion of a surgical system.

FIG. 8 illustrates a schematic view of a portion of a surgical system. The surgical system 800 can be similar to the surgical systems discussed above. The surgical system 800 can include a dedicated circuit for the sensor and a switching electrode 848. Any of the surgical systems discussed above or below can be modified to include the components of the surgical system 800.

Figure 9:
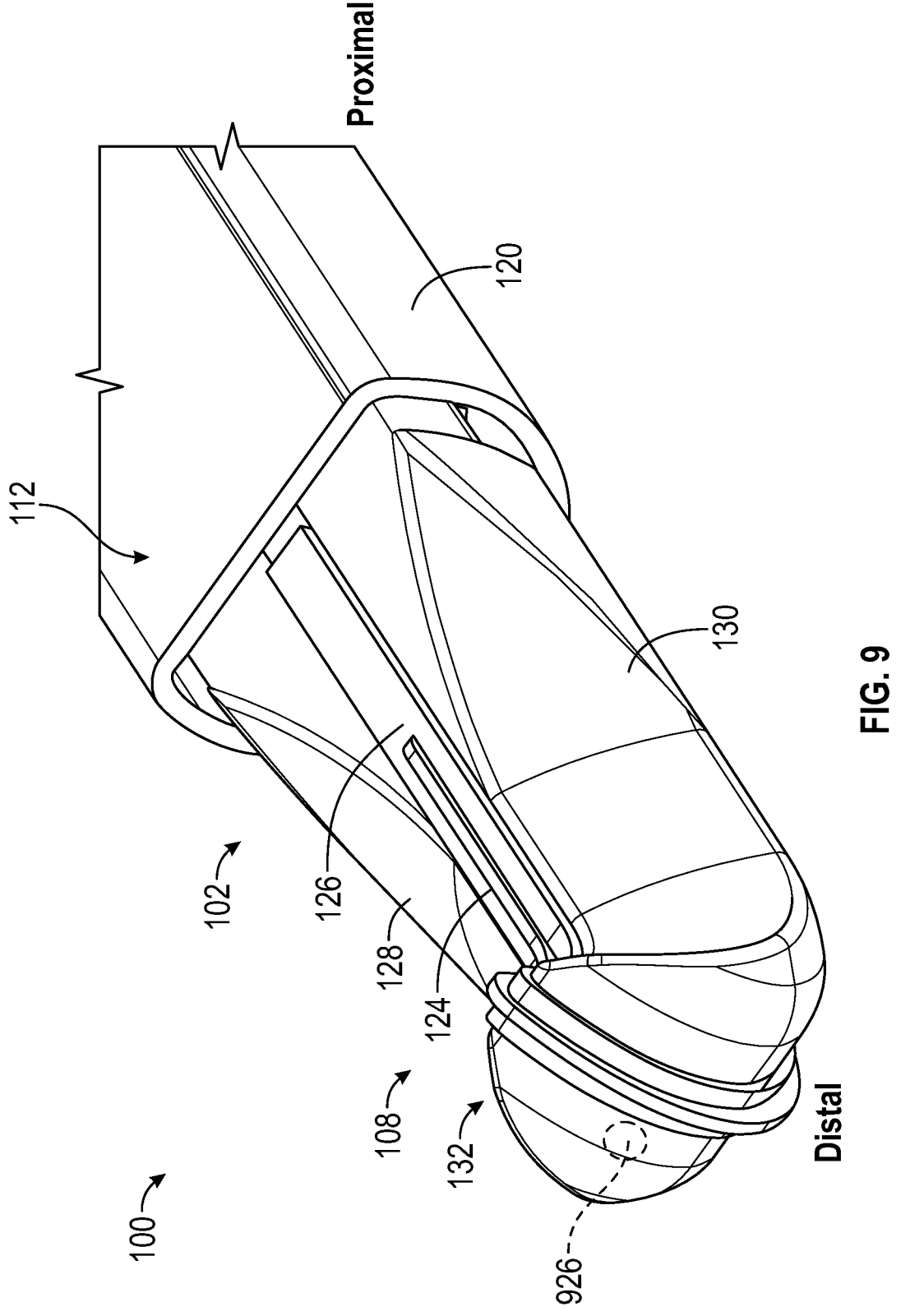
FIG. 9 illustrates an isometric view of a portion of a surgical system.
Figure 10:
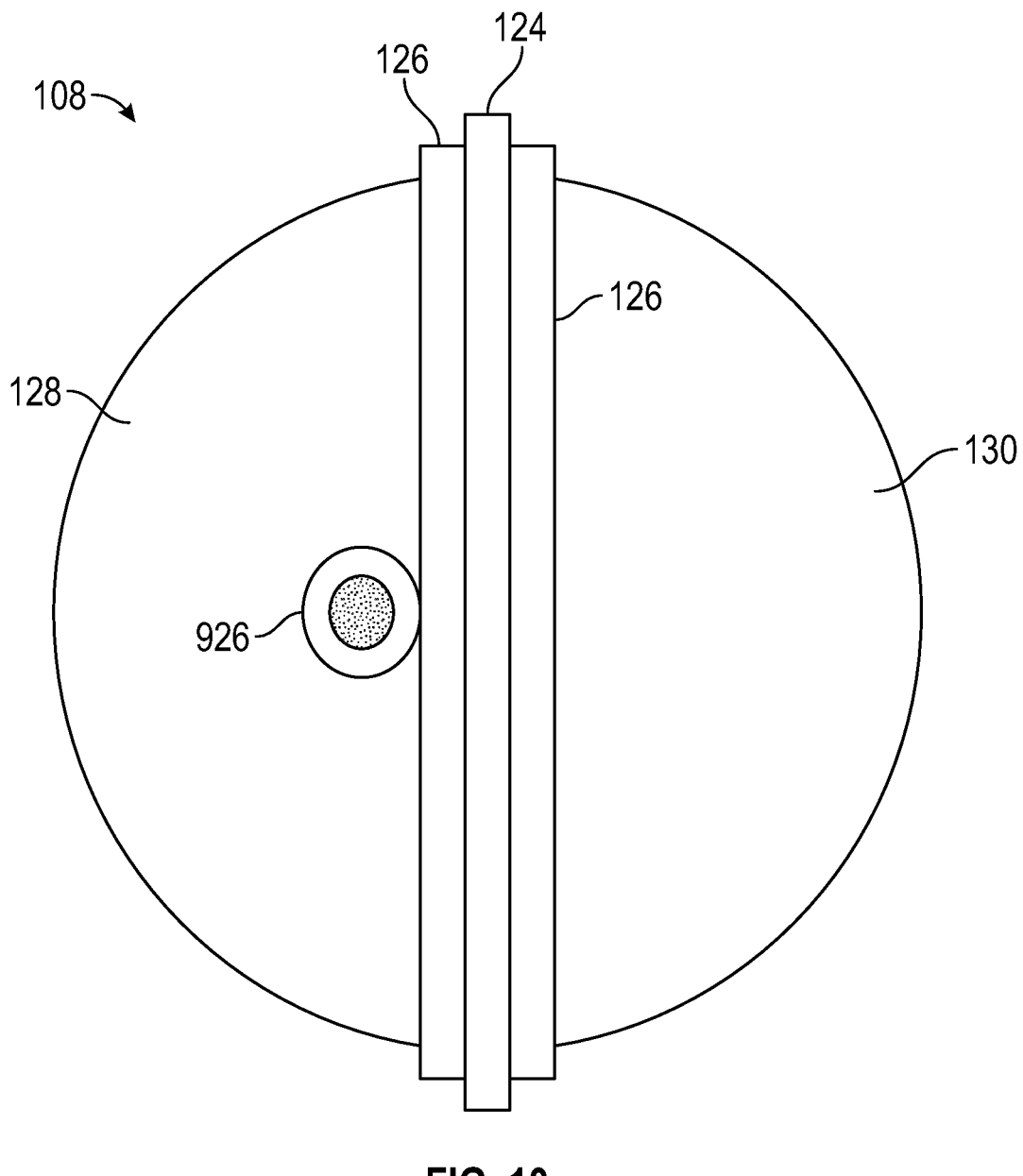
FIG. 10 illustrates a cross-sectional view of an end effector of a surgical system.

FIG. 9 illustrates an isometric view of a surgical system 100 including a surgical instrument 102 and shows orientation indicators Proximal and Distal. FIG. 10 illustrates a cross-sectional view of the end effector 108. FIGS. 9 and 10 are discussed together below. The surgical instrument 102 can be consistent with the instrument 102 discussed with respect to FIG. 1 of the surgical system 100 discussed above; FIGS. 9 and 10 show additional details of the surgical instrument 102.

For example, FIG. 9 shows that the end effector 108 can be connected to a distal portion of a shaft 120 of the intermediate portion 112. FIG. 9 also shows that the end effector 108 can include an active electrode 124, an insulator 126, a return electrode 128, and a return electrode 130. Together, the active electrode 124, the insulator 126, the return electrode 128, and the return electrode 130 can form a cutting tip 132 that can be operable (e.g., using the handpiece 110) to cut or resect tissue.

The active electrode 124 can be a conductor made of one or more conductive materials, such as copper, silver, aluminum, platinum, gold, steel alloys, or the like. The active electrode 124 can be relatively thin to deliver a high current density from the generator 104 to tissue for efficient cutting and sealing of tissue. The return electrodes 128 and 130 can also be constructed of one or more conductive materials. The active electrode 124 can be at least partially surrounded by the insulator 126, which can be a dielectric made of one or more insulative materials such as a ceramic, polymer, rubber, glass composites, or the like. The active electrode 124 can be or can include a heat-generating element, such as an RF sealing or other RF device, an electrosurgical cutting element, a resistive cutting element, a plasma-based device, laser device, ultrasonic device, or the like.

The insulator 126 can be sized and shaped to space the active electrode 124 away from the return electrodes 128 and 130 such as to optimize cutting and sealing efficiency and effectiveness while helping to limit overheating of the cutting tip 132 and helping to limit arcing directly from the active electrode 124 to the return electrode 128 or the return electrode 130, helping to ensure electric power flows from the active electrode 124 to tissue before returning to the return electrode 128 or the return electrode 130. The active electrode 124, the insulator 126, the return electrode 128, and the return electrode 130 can be sized and shaped to form the cutting tip 132 that can be a hook or a J-hook cutting tip (or to have a hook shape or a J-hook shape), which can be a useful or efficient shape for cutting or resecting or sealing tissue electrosurgically.

The return electrodes 128 and 130 can be on laterally opposite sides of the active electrode 134 and the insulator 126. The return electrode 128 and the return electrode 130 can be relatively large to help dissipate or reject heat and to help ensure there is adequate contact between the return electrode 128 and the return electrode 130 and tissue being cut or resected. Heat from the return electrode 128 can be transferred back to the handpiece 110 through the intermediate portion 112 (or the shaft 120) such as through one or more heat sinks. Optionally, a volume of the return electrode (128 or 130) can be at least 3 times larger than a volume of the active electrode 134.

As shown in FIGS. 9 and 10, the surgical instrument 102 can include a sensor 926 connected to or in communicative contact with the return electrode 128 (or the return electrode 130). For example, the sensor 926 can be a temperature sensor, such as a thermocouple, connected to the return electrode 128 or thermally coupled to the return electrode 128 (or the return electrode 130). The sensor 926 can be embedded in the return electrode 128 or can extend at least partially through the return electrode 128.

In operation, the sensor 926 can produce or generate a data signal based on one or more characteristics of the return electrode 128, the insulator 126, tissue near the end effector 108, or other component(s) of the end effector 108. The data signal can be transmitted from the sensor 926 to a generator (e.g., the generator 104), optionally when power to the active electrode 124 is reduced, such as for a period or increment of time. During such a reduced power period, the generator can use the data signal to determine one or more characteristic of the return electrode 128, the return electrode 130, the insulator 126, the active electrode 124, adjacent or nearby tissue, or other component of the end effector 108. Based on the determination, the generator 104 can adjust power delivered to the active electrode 124.

Figure 11:
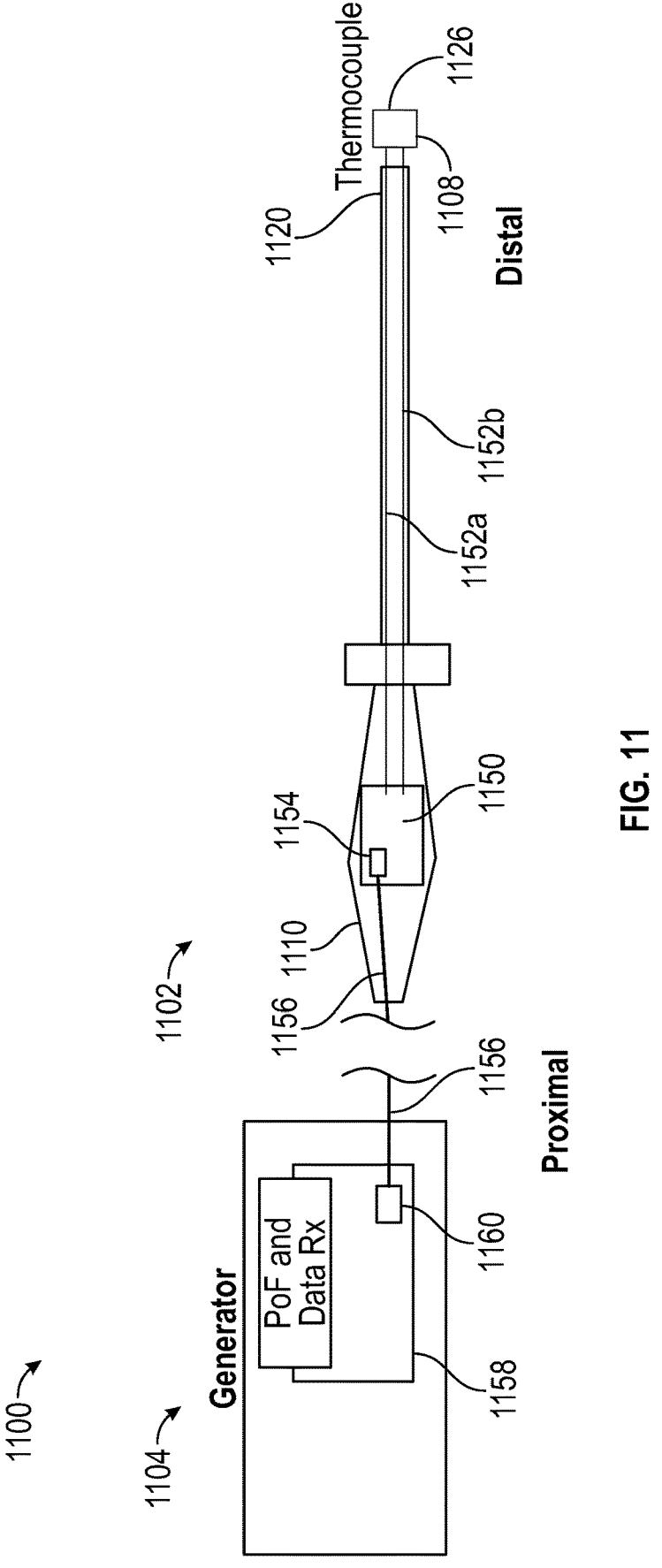
FIG. 11 illustrates a schematic view of a portion of a surgical system.

For example, when the sensor 926 is a temperature sensor, the generator 104 can determine a temperature of the return electrode 128 or the insulator 126, such as based on a temperature signal from the sensor 926, optionally during a period or interval of reduced power to the active electrode 124. When the generator 104 determines that the temperature of the return electrode 128 (or other component) is beyond a first threshold temperature, the generator 104 can reduce (or otherwise alter) the power delivered to the active electrode 124, which can help to reduce damage to the tissue, ineffective tissue cutting or coagulation, or damage to the end effector 108. Optionally, when the generator 104 determines, such as during a subsequent temperature determination period, that the temperature has fallen below a second threshold (which can be the same as the first threshold or lower or higher), the generator 104 can allow the power to resume to previous levels before the power was reduced. The surgical instrument 102 is one example of an instrument that can be incorporated into any of the surgical systems discussed above or below FIG. 11 illustrates a schematic view of a portion of a surgical system 1100. The surgical system 1100 can be similar to the surgical systems discussed above; the surgical system 1100 can include an optical conductor or fiber, which can be less susceptible to noise or interference. Any of the surgical systems discussed above or below can be modified to include the features of the surgical system 1100.

More specifically, the surgical system 1100 can include a surgical device 1102 and a generator 1104. The surgical device 1102 can include a handpiece 1110, a shaft 1120 connected to the handpiece 1110, and an end effector 1108 connected to a distal portion of the shaft 1120. The handpiece 1110 can include a controller 1150, which can be one or more circuits, control boards, processors, or the like configured to receive, process, and transmit signals. The end effector 1108 can include a sensor 1126 connected to the controller 1150 by one or more of conductors 1152a and 1152b. The sensor 1126 can be a sensor connected to conductors 1152a and 1152b to connect the sensor 1126 to the controller 1150. The controller 1150 can include a transceiver 1154 connected to an optical fiber 1156. The optical fiber 1156 can be connected to an optical controller 1158 of the generator 1104, which can include a transceiver 1160. Optionally, controller 1150 can be powered by the optical fiber (power over fiber), such as to help reduce a number of terminals used in the generator 1104 and a number of conductors used between the controller 1150 and the generator 1104.

In operation, the sensor 1126 can be configured to generate and transmit an electrical signal through the conductors 1152a and 1152b to the controller 1150. The controller 1150 can convert the electrical signal(s) to optical signal(s), which can be transmitted by the transceiver 1154 over the optical fiber 1156 to the transceiver 1160 where the optical controller 1158 can process the signal or transmit the signal to one or more other controllers of the generator 1104. In such an arrangement, noise generated by power within the handpiece 1110 and the connecting cables (e.g., the conductors 106) can have a reduced effect on the signal traveling through the optical portions of the surgical system 1100, such as the signal within the optical fiber 1156. This can allow the generator 1104 to more accurately determine a characteristic of the end effector 1108 or tissue, even when power is delivered to the end effector 1108, such as an active electrode thereof.

Figure 12:
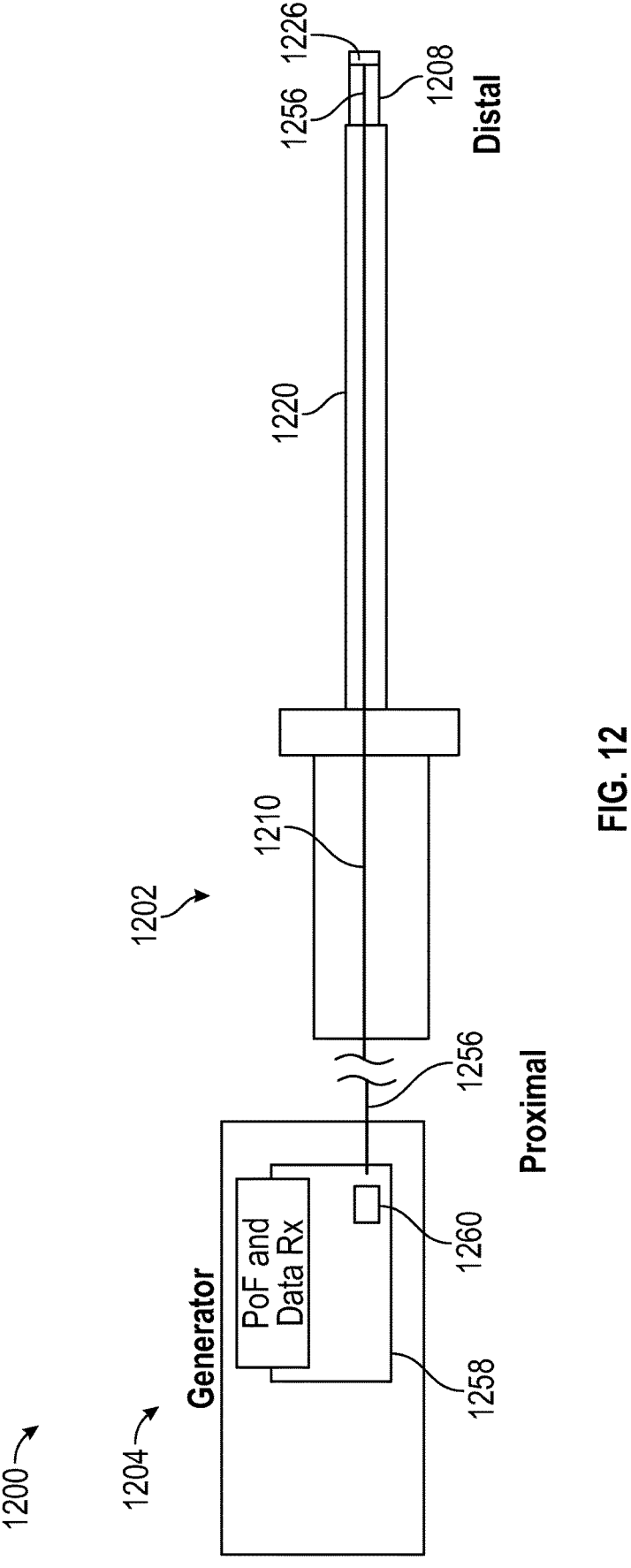
FIG. 12 illustrates a schematic view of a portion of a surgical system.

FIG. 12 illustrates a schematic view of a portion of a surgical system 1200. The surgical system 1200 can be similar to the surgical systems discussed above; the surgical system 1100 can include an optical sensor, which can be less susceptible to noise or interference. Any of the surgical systems discussed above or below can be modified to include the features of the surgical system 1200.

More specifically, the surgical system 1200 can include a surgical device 1202 and a generator 1204. The surgical device 1202 can include a handpiece 1210, a shaft 1220 connected to the handpiece 1210, and an end effector 1208 connected to a distal portion of the shaft 1220. The end effector 1208 can include a sensor 1226 connected to the generator 1204 by an optical fiber 1256. The optical fiber 1156 can be connected to an optical controller 1258 of the generator 1204, which can include a transceiver 1260.

Optionally, the sensor 1226 can be an optical ring resonator that can change its resonance frequency based on temperature (dependent of the waveguide or substrate material). Optionally, the sensor 1226 can be a Fibre bragg gating sensor that can produce a temperature signal based on strain in the optical material. Optionally, the sensor 1226 can be a material such as Gallium arsenide, Cadmium telluride, Silicon, or the like that can change in its optical parameters such as absorption, transmission, and reflection qualities with variation in temperature.

In operation, the sensor 1226 can be configured to generate and transmit an optical signal through the optical fiber 1256 to the controller 1258. The controller 1258 can convert the optical signal(s) and can process the signal(s) or transmit the converted signal to one or more other controllers of the generator 1204. In such an arrangement, noise generated by power within the end effector 1208, the shaft 1220, the handpiece 1210 and the connecting cables (e.g., the conductors 106) can have a reduced effect (or no effect) on the signal traveling through the optical portions of the surgical system 1200, such as the signal within the optical fiber 1256. This can allow the generator 1204 to determine one or more characteristic of the end effector 1208 (or components thereof, such as a return electrode) or nearby tissue without reducing or without interrupting power supplied to the end effector 1208 (such as to an active electrode thereof).

Figures 13, 14:
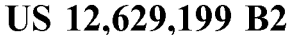
FIG. 13 illustrates a perspective view of a portion of a surgical system.
FIG. 14 illustrates a perspective view of a portion of a surgical system.

FIG. 13 illustrates a perspective view of a surgical instrument 1302, which can be a portion of any of the systems discussed above. The surgical instrument 1302 can be configured similarly to the surgical instruments discussed above. The surgical instrument 1302 can include an optical sensor and fiber. Any of the surgical instruments or surgical systems discussed above or below can be modified to include the features of the surgical instrument 1302.

The surgical instrument 1302 can be similar to the surgical instrument 102 discussed above, particularly with reference to FIG. 9. FIG. 13 shows that the surgical instrument 1302 can include an optical fiber 1356 extending at least partially through a shaft 1320 and connected to a sensor 1326. The sensor 1326 can be an optical sensor (as discussed above) or can be an exposed portion of the optical fiber 1356. The sensor 1326 can be connected to a top portion of an end effector 1308 such as to expose the sensor 1326 to tissue adjacent the end effector 1308, which can allow the sensor 1326 to produce a signal indicative of a characteristic, such as temperature, of the end effector 1308 or the tissue adjacent the end effector 1308, such as near an active electrode of the end effector 1308.

FIG. 14 illustrates a perspective view of a surgical instrument 1402, which can be a portion of any of the systems discussed above. The surgical instrument 1402 can be configured similarly to the surgical instruments discussed above. The surgical instrument 1402 can include an optical sensor and fiber. Any of the surgical instruments or surgical systems discussed above or below can be modified to include the features of the surgical instrument 1402.

The surgical instrument 1402 can be similar to the surgical instrument 1302 discussed above. FIG. 14 shows that the surgical instrument 1402 can include an optical fiber 1456 extending at least partially through a shaft 1420 and connected to a sensor 1426. The sensor 1426 can be an optical sensor (as discussed above) or can be an exposed portion of the optical fiber 1456. The sensor 1426 can be located within an end effector 1408 of the surgical instrument 1402, such as to expose the sensor 1426 to the end effector 1408, which can allow the sensor 1426 to produce a signal indicative of a characteristic, such as temperature, of the end effector 1408, such as an active electrode or return electrode. In this way, exposure of the sensor 1426 to an environment can be limited while still allowing the sensor 1426 to generate a signal corresponding to one or more characteristic of the end effector 1408.

Figure 15:
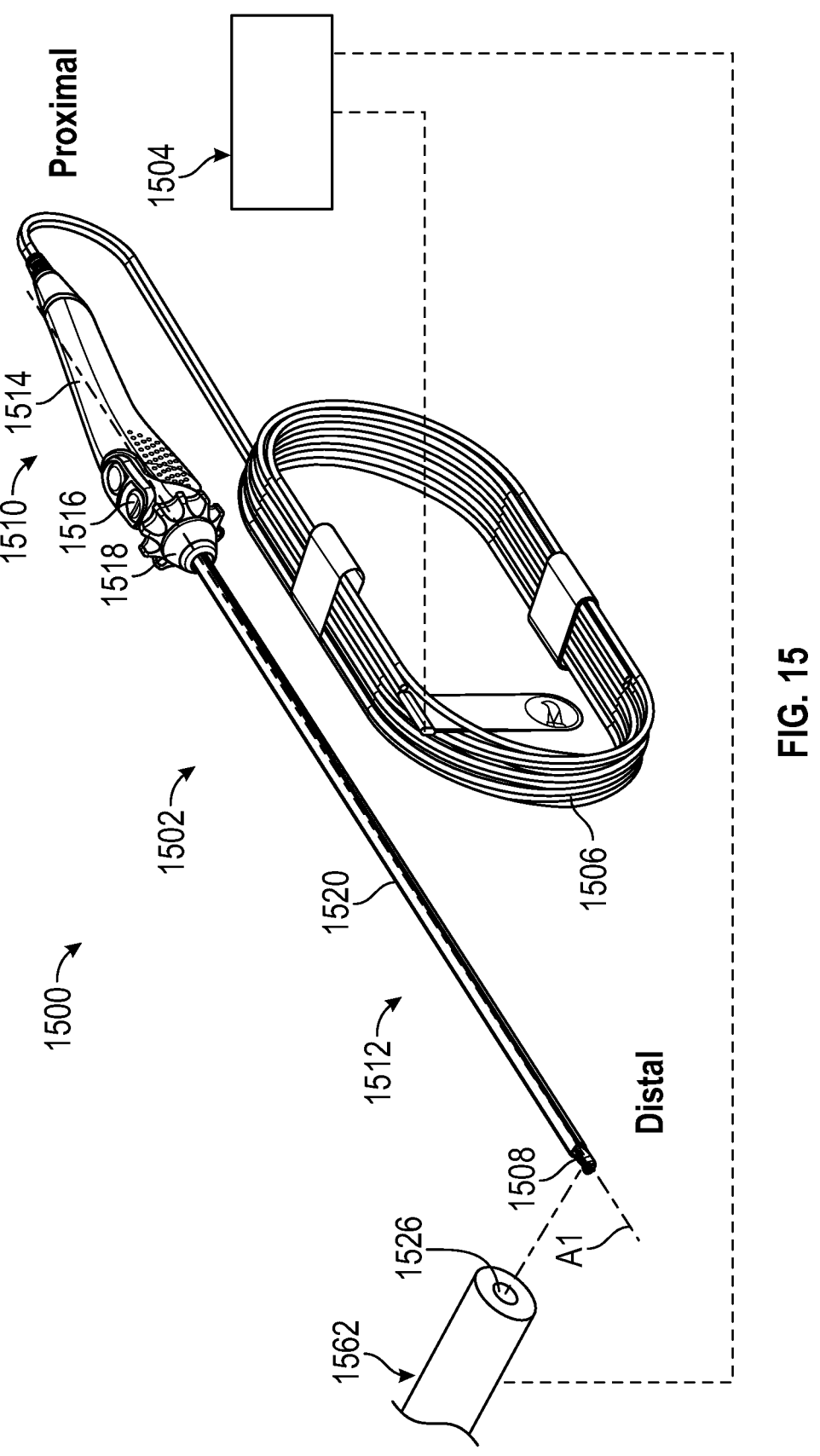
FIG. 15 illustrates an isometric view of a surgical system.

FIG. 15 illustrates an isometric view of a surgical system 1500. The surgical system 1500 can be similar to the surgical instruments discussed above. The surgical system 1500 can include an independent optical sensor. Any of the surgical instruments or surgical systems discussed above or below can be modified to include the features of the surgical system 1500.

The surgical system 1500 can include a surgical instrument 1502 that can be connected to a generator 1504, such as via one or more wires or conductors 1506. The generator

1504 can be similar to the generator 104 (or other generator) discussed above. The surgical instrument 1502 can be similar to the surgical instrument 102 (or other surgical device) discussed above and can include an end effector 1508, a handpiece 1510, and an intermediate portion 1512. The handpiece 1510 can include a housing 1514, controls 1516, and a rotational actuator 1518. FIG. 1 also shows orientation indicators Proximal and Distal and a longitudinal axis A1.

The surgical instrument 1502 can also include an optical instrument 1562, such as a scope (e.g., an endoscope). The optical instrument 1562 can be connected to the generator 1504. The optical instrument 1562 can be independent of the surgical instrument 1502 but can be configured to be used together with the surgical instrument 1502. The surgical instrument 1502 can include a sensor 1526 that can be an optical sensor, electrical sensor, or the like. The sensor 1526 can be configured to produce a data signal based on one or more characteristics of the surgical instrument 1502 (e.g., the end effector 1508) or tissue near the end effector 1508. In some examples, the sensor 1526 can be an infrared sensor configured to generate a signal corresponding to a temperature of objects in a field of view of the sensor 1526.

Because the sensor 1526 is separated from the end effector 1508, power delivered by the generator 1504 to the end effector 1508 (such as for cutting operations), can have a minimal or reduced effect on the data signal generated by the sensor 1526 and transmitted to the generator 1504, allowing the generator 1504 to determine, more accurately, one or more characteristics of the end effector 1508 or nearby tissue, even when the generator 1504 is delivering power to the end effector 1508.

Figure 16:
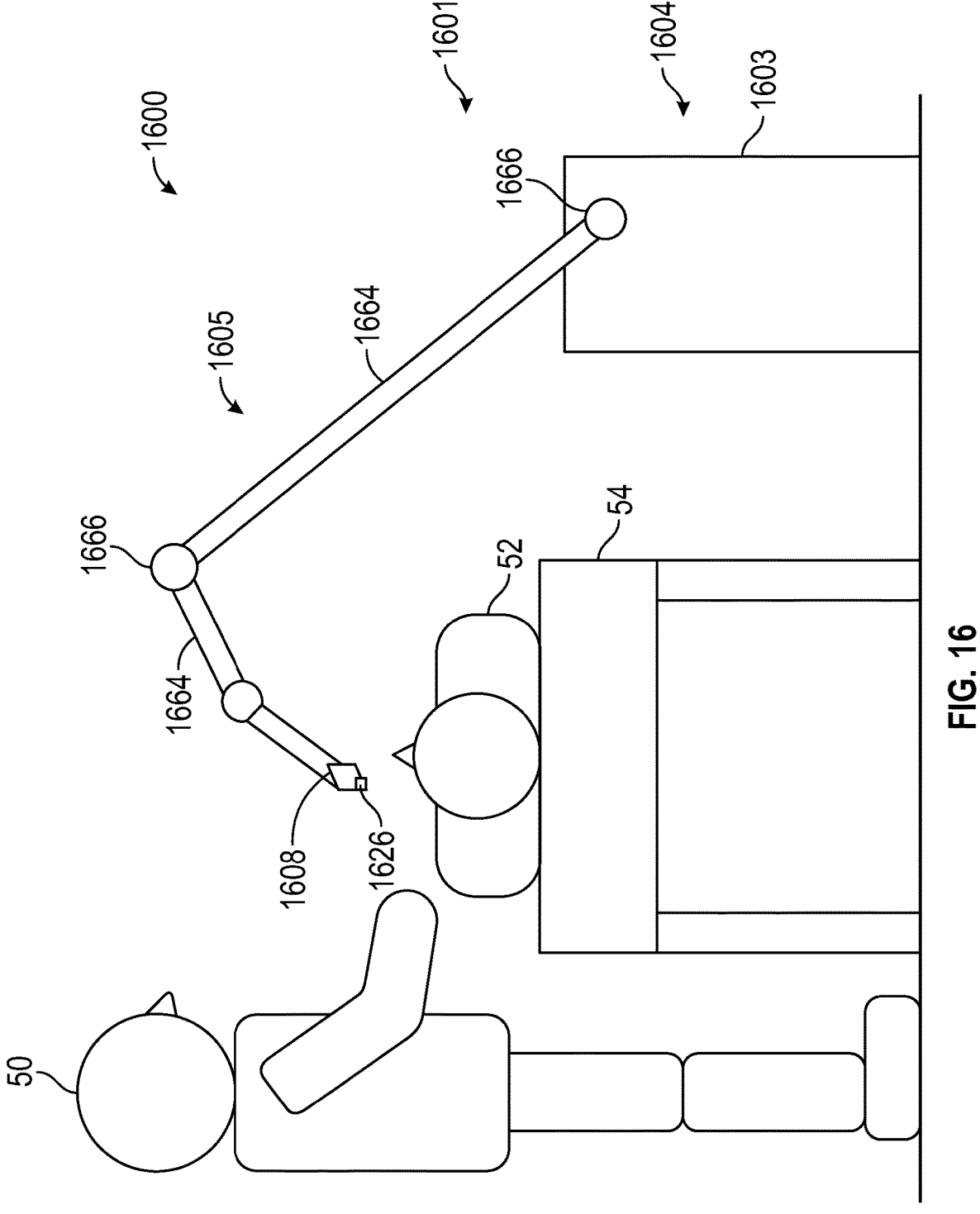
FIG. 16 illustrates an isometric view of a surgical system.

FIG. 16 illustrates an isometric view of a surgical system 1600. The systems, devices, and methods discussed above (or below), such as in regard to end effectors and sensors, can be provided in hand-held, hand-operated devices, as discussed above. Further, the systems, devices, and methods discussed herein can also be employed in surgical robots as well.

For example, a surgical system 1600 can include a robot 1601. The robot 1601 can generally be a multi-link structure operable to move an end effector. For example, the robot 1601 can include a control system 1603, which can optionally include a generator 1604 (similar to the generator 104, for example). The robot 1601 can also include an arm 1605 comprised of a plurality of links 1664 that can be connected to one another by joints or joint units 1666.

The robot 1601 can also include an end effector 1608 connected to a distal portion of the arm 1605 where a sensor 1626 can be connected to the end effector 1608 or other portion of the arm 1605. The end effector 1608 can include, but is not limited to, any end effector described herein. Further, the sensor 1626 can include any suitable sensor or data transmission aspect described herein, such as any of the sensor 226 or the sensor 326. The robot 1601 can also include one or more actuators located either in the of joint units 1666 or in the control system 1603. The joint units 1666 can be controlled, e.g., by the control system 1603 or a surgeon 50, to move the links 1664 and the end effector 1608 to perform a procedure, a portion of a procedure, or to assist with at least a portion of a procedure, such as on a patient 52 on a table 54.

Reducing heatsink size or volume can provide a less bulky and more refined end effector tip (e.g., a thinner tip or a tip with a reduced cross-section). For robotic surgery, where there can be limited space between the end of the device and an articulating element of the robot (e.g., the end effector 1608) a thinner or smaller tip can help allow smoother or easier operation of the arm and the electrosurgical device. By using the methods discussed above (or below) for controlling or adjusting power to help prevent thermal runaway or overheating of the end effector 1608, smaller return electrodes or other components can be used in the end effector 1608, allowing the end effector 1608 to be smaller and more precise or maneuverable, helping to improve performance of the robot 1601.

Figure 17:
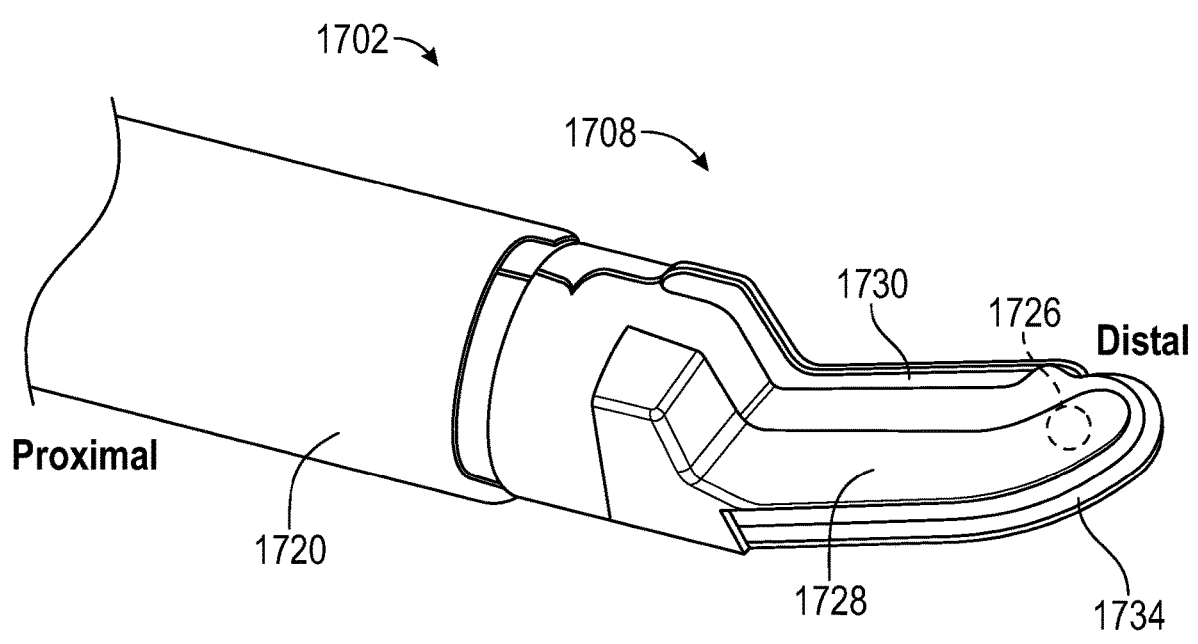
FIG. 17 illustrates an isometric view of a portion of a surgical system.

FIG. 17 illustrates an isometric view of a surgical instrument 1702, which can include a surgical spatula. More specifically, the surgical instrument 1702 can include an end effector 1708 connected to a shaft 1720. The end effector 1708 can include an active electrode 1734 and return electrodes 1728 and 1730, which can be separated by one or more insulators. The end effector 1708 can also include a sensor 1726 that can be configured to produce a data signal based on a condition of the return electrode 1728, the return electrode 1730, the active electrode 1734, other portion of the end effector 1708, or nearby tissue. The sensor 1726 can be connected to a generator (e.g., the generator 104) such as to transmit the data signal thereto, allowing the generator to control operation of the surgical instrument 1702 based at least in part on the data signal, as discussed above.

Figure 18:
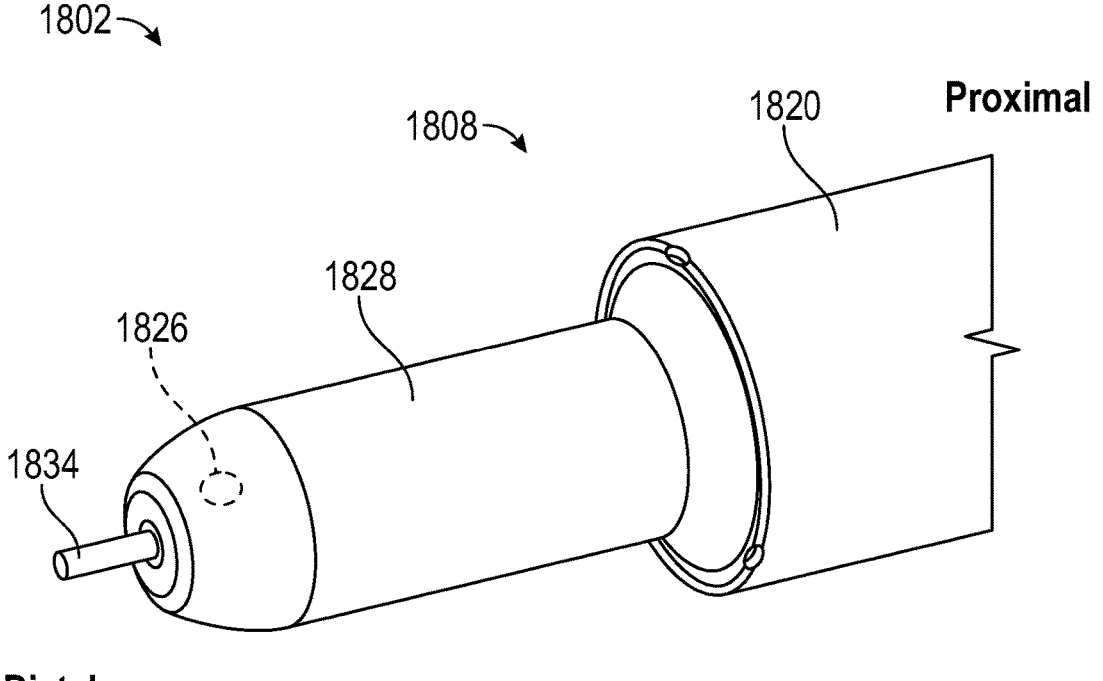
FIG. 18 illustrates an isometric view of a portion of a surgical system.

FIG. 18 illustrates an isometric view of a surgical instrument 1802, which can include a surgical pencil. More specifically, the surgical instrument 1802 can include an end effector 1808 connected to a shaft 1820. The end effector 1808 can include an active electrode 1834 and a return electrode 1828, which can be separated by one or more insulators. The end effector 1808 can also include a sensor 1826 that can be configured to produce a data signal based on a condition of the return electrode 1828, the active electrode 1834, other portion of the end effector 1808, or nearby tissue. The sensor 1826 can be connected to a generator (e.g., the generator 104), allowing the generator to control operation of the surgical instrument 1802 based at least in part on the data signal, as discussed above.

Figure 19:
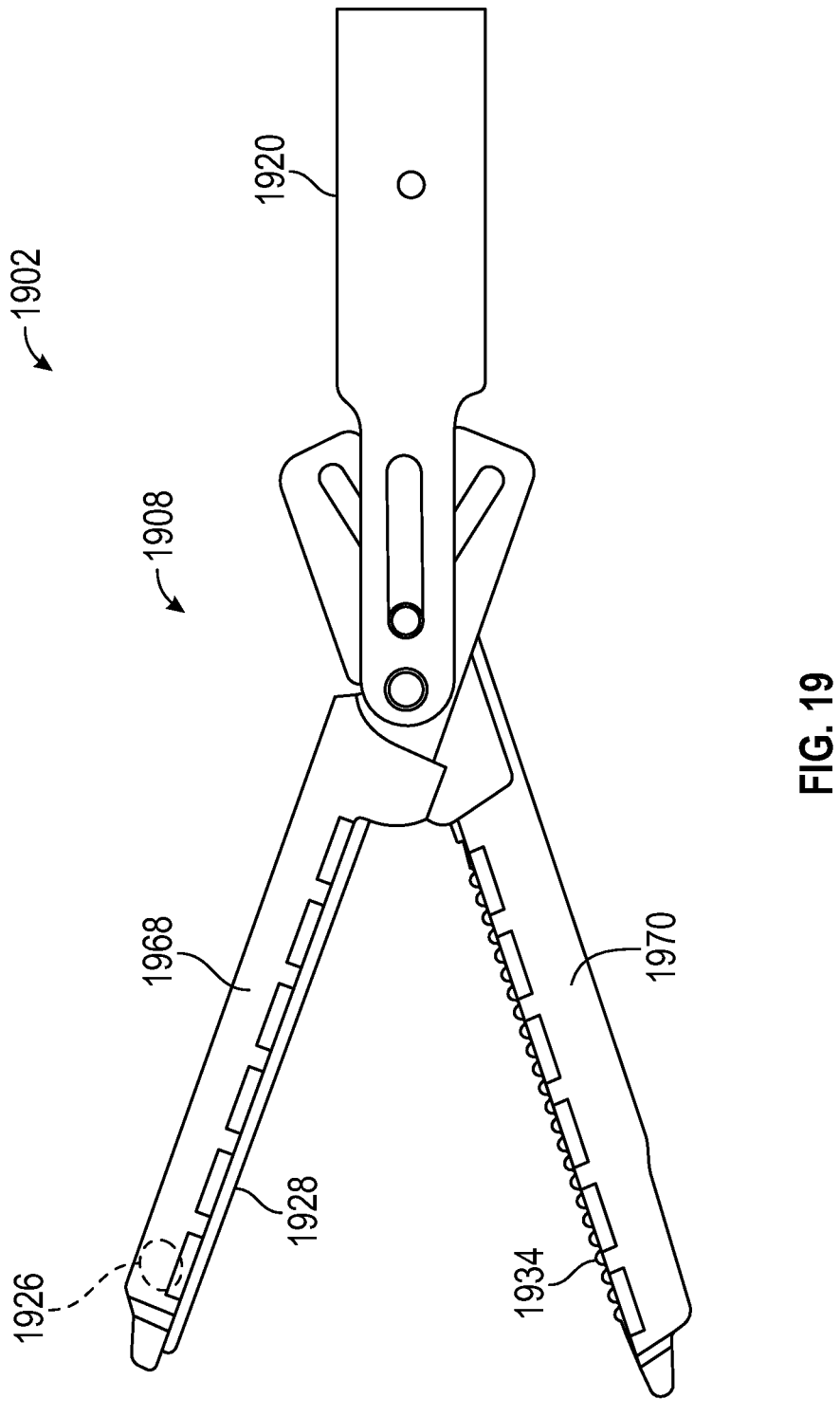
FIG. 19 illustrates an isometric view of a portion of a surgical system.

FIG. 19 illustrates an isometric view of a surgical instrument 1902, which can include a forceps. More specifically, the surgical instrument 1902 can include an end effector 1908 connected to a shaft 1920. The end effector 1908 can include jaws 1968 and 1970, where one or more of the jaws 1968 and 1970 can be movable with respect to each other or the shaft 1920, such as to grasp tissue. The surgical instrument 1902 can optionally include a movable cutting blade. The jaw 1968 can include one or more return electrodes 1928 and a sensor 1926. The jaw 1970 can include an active electrode 1934. Optionally, each of the jaws 1968 and 1970 can include an active electrode and a return electrode. The sensor 1926 can be connected to a generator (e.g., the generator 104) and configured to produce a data signal based on a condition of the return electrode 1928, the active electrode 1934, other portion of the end effector 1908, or nearby tissue, allowing the generator to control operation of the surgical instrument 1902 based at least in part on the data signal, as discussed above.

The methods and systems discussed above with regard to sensor and data transmission aspects described herein can be employed in any type of electrosurgical device. These aspects can be employed in any suitable electrosurgical device to improve the device, such as an electrosurgical spatula (FIG. 17), a pencil (FIG. 18), a forceps (FIG. 19) or another monopolar or bipolar electrosurgical device that includes a sensor configured to generate a signal based on a device or tissue characteristic. Similarly, the sensor types described herein, as well as other sensor types not described herein, can be used with the data transmission features described herein to overcome the challenges with radiofrequency induced interference on sensor data transmission in electrosurgical devices. Any sensor, such as a temperature sensor, a force sensor, a pressure sensor, and angle sensor, a proximity sensor, a contact sensor, an amount of tissue sensor, or the like can be used in any suitable device for the sensor type, and the data transmission aspects described herein can be used to overcome interference caused by the particular radiofrequency treatment modalities that cause the interference.

Figure 20:
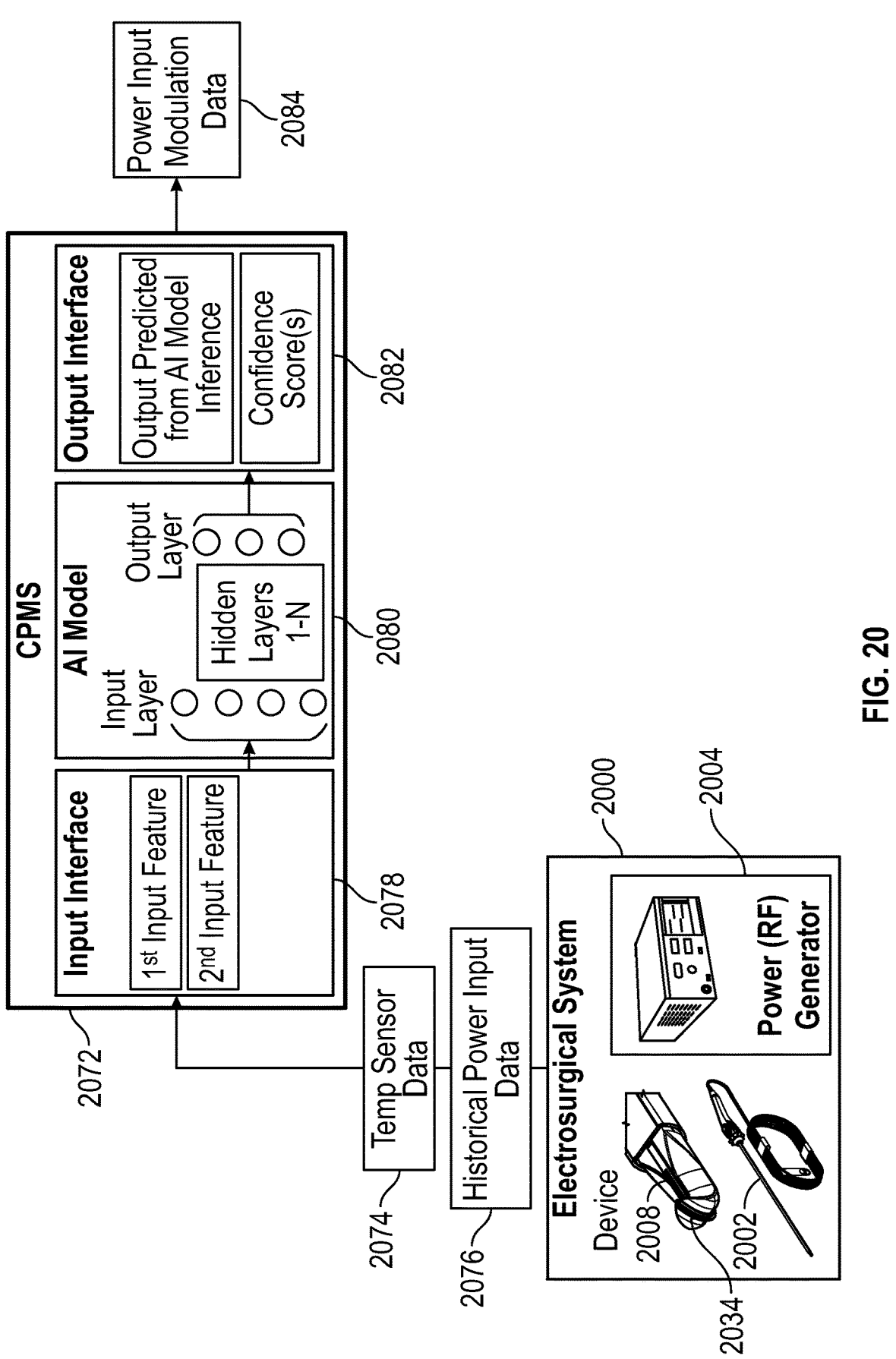
FIG. 20 illustrates a schematic view of a surgical system.

FIG. 20 shows a schematic diagram of an exemplary computer-based power management system (CPMS) 2072 that can be configured to adjust a power input to an active electrode 2034 of an electrosurgical device 2002 (including an end effector 2008) based on temperature sensor data 2074 or power input data 2076 that is collected during an electrosurgical cutting procedure.

For example, in embodiments the temperature sensor data 2074 can include temperature measurements taken at a predetermined sampling rate (e.g., every 100 milliseconds, in a range between every 100 milliseconds-1000 milliseconds, or perhaps between every 100-500 milliseconds). The sampling time can be dependent on the device and sensor type, and the sampling time can be configured to retrieve a reliable temperature sensor data signal without an excessive impact on the delivery of power to the active electrode of the electrosurgical device 2002.

The power input data 2076 can be received from or within the power generator 2004, which can be similar to the generator 104 or other generator discussed above. The power input data 2076 can correspond to a waveform signal that is supplied to the active electrode 2034 of the end effector 2008 of the electrosurgical device 2002.

In various embodiments, the computer-based power management system 2072 can include an input interface 2078 through which the temperature sensor data 2074 and the power input data 2076 can be provided as input features to an artificial intelligence (AI) model 2080, which can perform one or more inference operations in which the temperature sensor data 2074 and the power input data 2076 can be applied to the AI model 2080 to modulate the power input to the active electrode of the electrosurgical device 2002.

In some embodiments, the input interface 2078 may be a direct data link between the computer-based power management system 2072 and the electrosurgical system 2000 that generates at least some of the input features. For example, the input interface 2078 can transmit the temperature sensor data 2074 or the power input data directly to the computer-based power management system during a therapeutic or diagnostic medical procedure.

In some embodiments, a first input feature can be a sliding total power input window generated from the historical power input data 2076 received from the power generator 2004. For example, the historical power input data 2076 can be used to continually generate indications of total power input to the active electrode within a predetermined rearward looking window of time. As a specific but non-limiting example, an indication in the sliding total power input window can indicate the amount of power that was delivered to the active electrode during the last 3 seconds of time.

In some embodiments, a second input feature can include one or more discrete temperature measurements obtained via a temperature sensor configured to measure a temperature of the return electrodes. In this example, the second input feature may be the raw temperature sensor data 2074. Additionally, or alternatively, the second input feature can include an indication of a rate of change of the temperature measurements or a rate of change over a period of time (e.g., an acceleration of the rate of temperature change).

Based on one or more of the above input features, the computer-based power management system 2072 can perform an inference operation using the AI model 2080 to generate power input modulation data 2084 that can be used to modulate (e.g., adjust, reduce) power input to the active electrode. For example, the input interface 2078 can deliver the temperature sensor data 2074 and the historical power input data 2076 into an input layer of the AI model 2080 that can propagate these input features through the AI model 2080 to an output interface 2082 (or output layer). The AI model 2080 can provide a computer system the ability to perform tasks, without explicitly being programmed, by making inferences based on patterns found in the analysis of data. AI model 2080 explores the study and construction of algorithms (e.g., machine-learning algorithms) that may learn from existing data and make predictions about new data. Such algorithms operate by building an AI model 2080 from example training data in order to make data-driven predictions or decisions expressed as outputs or assessments.

Two common modes for machine learning (ML) are: supervised ML and unsupervised ML. Supervised ML can use prior knowledge (e.g., examples that correlate inputs to outputs or outcomes) to learn the relationships between the inputs and the outputs. One goal of supervised ML is to learn a function that, given some training data, best approximates the relationship between the training inputs and outputs so that the ML model can implement the same relationships when given inputs to generate the corresponding outputs. Unsupervised ML can include the training of an ML algorithm using information that is neither classified nor labeled, and allowing the algorithm to act on that information without guidance. Unsupervised ML can be useful in exploratory analysis because it can automatically identify structure in data.

Common tasks for supervised ML can include classification problems and regression problems. Classification problems, also referred to as categorization problems, aim at classifying items into one of several category values (for example, is this object an apple or an orange?). Regression algorithms aim at quantifying some items (for example, by providing a score to the value of some input). Some examples of commonly used supervised-ML algorithms are Logistic Regression (LR), Naive-Bayes, Random Forest (RF), neural networks (NN), deep neural networks (DNN), matrix factorization, and Support Vector Machines (SVM).

Some common tasks for unsupervised ML include clustering, representation learning, and density estimation. Some examples of commonly used unsupervised-ML algorithms are K-means clustering, principal component analysis, and autoencoders.

Another type of ML is federated learning (also known as collaborative learning) that trains an algorithm across multiple decentralized devices holding local data, without exchanging the data. This approach stands in contrast to traditional centralized machine-learning techniques where all the local datasets are uploaded to one server, as well as to more classical decentralized approaches which often assume that local data samples are identically distributed. Federated learning enables multiple actors to build a common, robust machine learning model without sharing data, thus allowing to address critical issues such as data privacy, data security, data access rights and access to heterogeneous data.

In some examples, the AI model 2080 may be trained continuously or periodically prior to performance of the inference operation by the computer-based power management system 2072. Then, during the inference operation, the patient specific input features provided to the AI model 2080 may be propagated from an input layer, through one or more hidden layers, and ultimately to an output interface 2082 that corresponds to the power input modulation data 2084.

During or subsequent to the inference operation, the power input modulation data 2084 can be communicated to the user via the user interface (UI) or automatically cause the generator which includes, or can be connected to, the computer-based power management system 2072 for performing a desired action. In some examples, if the temperature sensor data determines a characteristic of the temperature sensor data exceeded a defined parameter, such as exceeding a specified temperature for greater than a specified period of time defining an incident. The generator can record at least a portion of the temperature sensor data, the historical power input data 2076, the power input modulation data 2084, or occurrence of an incident to a memory. The incident data can be saved as an individual record, the record can include device identifying information or patient identifying information. The individual records or aggregated individual records can be transmitted to a memory for analysis.

Figure 21:
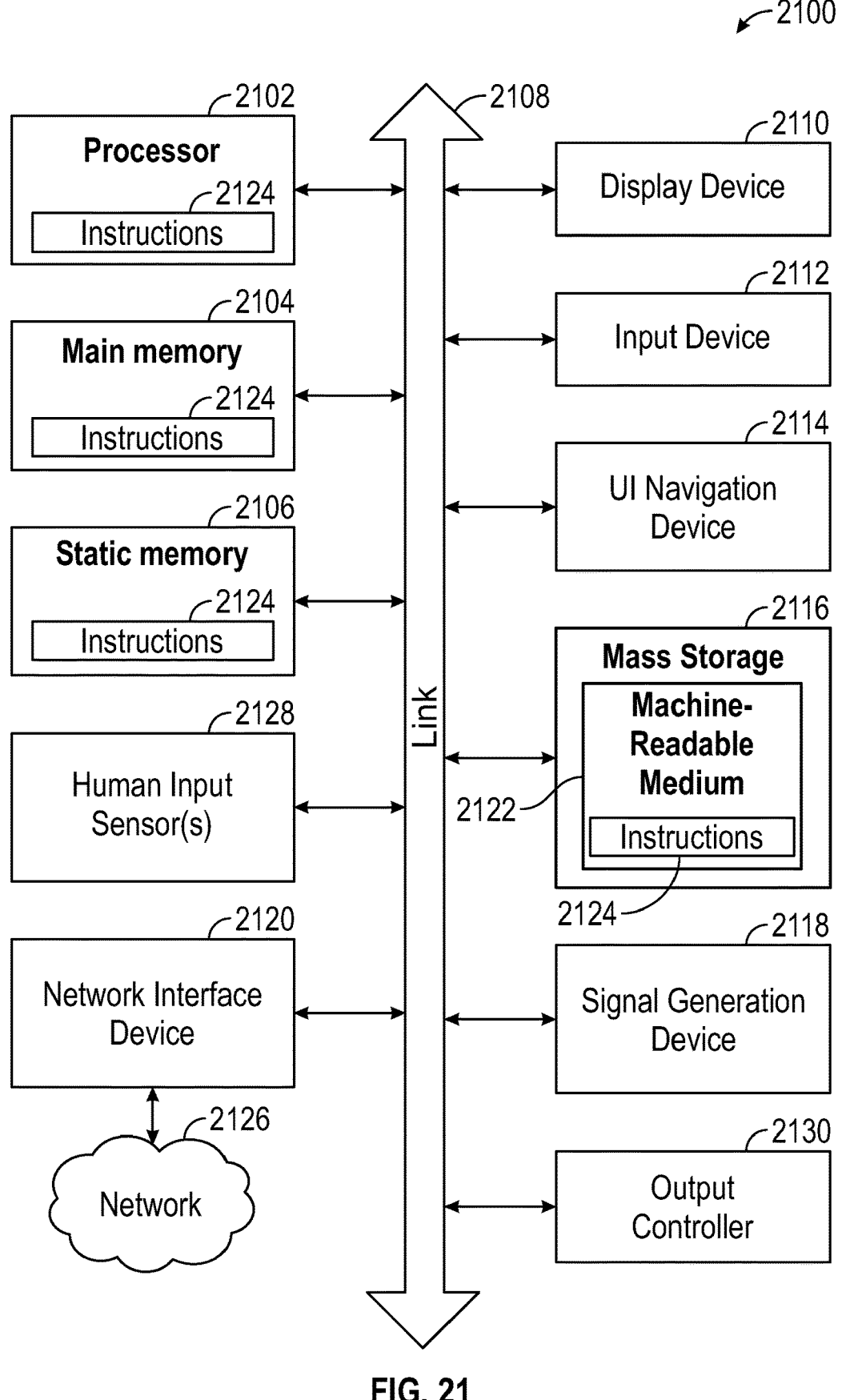
FIG. 21 illustrates a schematic view of an example of a machine upon which one or more embodiments may be implemented.

FIG. 21 illustrates a schematic view of an example machine 2100 upon which any one or more of the techniques (e.g., methodologies) discussed herein may perform. Examples, as described herein, may include, or may operate by, logic or a number of components, or mechanisms in the machine 2100. Circuitry (e.g., processing circuitry) is a collection of circuits implemented in tangible entities of the machine 2100 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 2100 follow.

In alternative embodiments, the machine 2100 may operate as a standalone device or may be connected (e.g., networked) to other machines. In a networked deployment, the machine 2100 may operate in the capacity of a server machine, a client machine, or both in server-client network environments. In an example, the machine 2100 may act as a peer machine in peer-to-peer (P2P) (or other distributed) network environment. The machine 2100 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 2100 may include a hardware processor 2102 (e.g., a central processing unit (CPU), a graphics processing unit (GPU), a hardware processor core, or any combination thereof), a main memory 2104, a static memory (e.g., memory or storage for firmware, microcode, a basic-input-output (BIOS), unified extensible firmware interface (UEFI), etc.) 2106, and mass storage 2108 (e.g., hard drive, tape drive, flash storage, or other block devices) some or all of which may communicate with each other via an interlink (e.g., bus) 2130. The machine 2100 may further include a display unit 2110, an alphanumeric input device 2112 (e.g., a keyboard), and a user interface (UI) navigation device 2114 (e.g., a mouse). In an example, the display unit 2110, input device 2112 and UI navigation device 2114 may be a touch screen display. The machine 2100 may additionally include a storage device (e.g., drive unit) 2108, a signal generation device 2118 (e.g., a speaker), a network interface device 2120, and one or more sensors 2116, such as a global positioning system (GPS) sensor, compass, accelerometer, or other sensor. The machine 2100 may include an output controller 2128, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 2102, the main memory 2104, the static memory 2106, or the mass storage 2108 may be, or include, a machine readable medium 2122 on which is stored one or more sets of data structures or instructions 2124 (e.g., software) embodying or utilized by any one or more of the techniques or functions described herein. The instructions 2124 may also reside, completely or at least partially, within any of registers of the processor 2102, the main memory 2104, the static memory 2106, or the mass storage 2108 during execution thereof by the machine 2100. In an example, one or any combination of the hardware processor 2102, the main memory 2104, the static memory 2106, or the mass storage 2108 may constitute the machine readable media 2122. While the machine readable medium 2122 is illustrated as a single medium, the term "machine readable medium" may include a single medium or multiple media (e.g., a centralized or distributed database, or associated caches and servers) configured to store the one or more instructions 2124.

The term "machine readable medium" may include any medium that is capable of storing, encoding, or carrying instructions for execution by the machine 2100 and that cause the machine 2100 to perform any one or more of the techniques of the present disclosure, or that is capable of storing, encoding or carrying data structures used by or associated with such instructions. Non-limiting machine readable medium examples may include solid-state memories, optical media, magnetic media, and signals (e.g., radio frequency signals, other photon based signals, sound signals, etc.). In an example, a non-transitory machine readable medium comprises a machine readable medium with a plurality of particles having invariant (e.g., rest) mass, and thus are compositions of matter. Accordingly, non-transitory machine-readable media are machine readable media that do not include transitory propagating signals. Specific examples of non-transitory machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 2124 may be further transmitted or received over a communications network 2126 using a transmission medium via the network interface device 2120 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 2120 may include one or more physical jacks (e.g., Ethernet, coaxial, or phone jacks) or one or more antennas to connect to the communications network 2126. In an example, the network interface device 2120 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 2100, and includes digital or analog communications signals or other intangible medium to facilitate communication of such software. A transmission medium is a machine readable medium.

NOTES AND EXAMPLES

The following, non-limiting examples, detail certain aspects of the present subject matter to solve the challenges and provide the benefits discussed herein, among others.

Example 1 is a method of controlling an electrosurgical system for treating a tissue, the method comprising: delivering power from a control system to an end effector to affect tissue; reducing the power delivered to the end effector; and receiving, from an electrical sensor when the power delivered to the end effector is reduced, a data signal indicative of at least one characteristic of the end effector or the tissue being treated by the end effector, wherein the power and the data signal are transmitted along a shared conductor.

In Example 2, the subject matter of Example 1 optionally includes 1rein the shared conductor is a portion of a 1-wire EEPROM circuit.

In Example 3, the subject matter of any one or more of Examples 1-2 optionally include wherein the control system is configured to determine a sensed parameter based on the data signal generated during a period of time when the power delivered to the end effector is reduced.

In Example 4, the subject matter of any one or more of Examples 1-3 optionally include wherein the control system is configured to reduce the power delivered to the end effector for a duration between 10 milliseconds and 100 milliseconds during an instance of measuring the data signal.

In Example 5, the subject matter of any one or more of Examples 1-4 optionally include producing a converted data signal when the delivered power is reduced.

In Example 6, the subject matter of Example 5 optionally includes wherein the converted data signal is produced using an analog to digital converter (ADC) connected to the sensor.

In Example 7, the subject matter of any one or more of Examples 1-6 optionally include wherein reducing the power delivered to the end effector includes reducing a radiofrequency energy delivered to the end effector.

In Example 8, the subject matter of any one or more of Examples 1-7 optionally include wherein reducing the power delivered to the end effector includes reducing a voltage delivered to the end effector.

In Example 9, the subject matter of any one or more of Examples 1-8 optionally include wherein reducing the power delivered to the end effector includes reducing a current delivered to the end effector.

In Example 10, the subject matter of any one or more of Examples 1-9 optionally include wherein the electrical sensor is a temperature sensor, and wherein the at least one characteristic is representative of the temperature of the end effector.

Example 11 is a surgical system comprising: a surgical device comprising: a hand piece operable to control the surgical device; and an end effector connected to the hand piece, the end effector comprising: an active electrode configured to deliver power to tissue; a return electrode configured to receive power from the tissue; and a temperature sensor configured to generate a temperature signal based on a temperature of the return electrode; and a control system connected to the active electrode, the return electrode, and the temperature sensor, the control system configured to adjust a power delivered to the active electrode based on the temperature signal of the return electrode.

In Example 12, the subject matter of Example 11 optionally includes wherein the control system is configured to reduce the power delivered to the active electrode while receiving the temperature signal.

In Example 13, the subject matter of any one or more of Examples 11-12 optionally include wherein the control system is configured to determine a temperature of the return electrode based on the temperature signal generated during a period of time when the power delivered to the active electrode is reduced.

In Example 14, the subject matter of any one or more of Examples 11-13 optionally include wherein the control system is configured to reduce the power delivered to the active electrode for a duration between 10 milliseconds and 100 milliseconds during an instance of measuring the temperature.

In Example 15, the subject matter of any one or more of Examples 11-14 optionally include wherein the return electrode includes a heat sink extending longitudinally between the end effector and the hand piece, the heat sink configured to transfer heat proximally away from the return electrode to cool the return electrode when the return electrode receives the power from the tissue.

In Example 16, the subject matter of any one or more of Examples 11-15 optionally include wherein a volume of the return electrode is larger than a volume of the active electrode.

In Example 17, the subject matter of Example 16 optionally includes times larger than the volume of the active electrode.

In Example 18, the subject matter of any one or more of Examples 11-17 optionally include wherein the temperature sensor is thermally coupled to the return electrode.

In Example 19, the subject matter of any one or more of Examples 11-18 optionally include a second return electrode, the second return electrode, the return electrode, and the active electrode and electrode extending along a longitudinal path, the return electrode and second return electrode located on laterally opposite sides of the active electrode, and an electrically insulative layer located at least partially between the active electrode and the return electrode, and located at least partially between the active electrode and the second return electrode.

In Example 20, the subject matter of any one or more of Examples 11-19 optionally include wherein the active electrode is connected to a first terminal of the control system, the temperature sensor is connected to a second terminal of the control system and a third terminal of the control system, and the return electrode is connected to the third terminal.

In Example 21, the subject matter of Example 20 optionally includes a converter located at least partially within the surgical device and connected to the second terminal and the third terminal, the converter configured to produce a converted temperature signal based on the temperature signal when the delivered power is reduced.

In Example 22, the subject matter of any one or more of Examples 11-21 optionally include wherein the temperature sensor comprises an optical sensor.

In Example 23, the subject matter of Example 22 optionally includes wherein the optical sensor is connected to the control system including by an optical fiber.

In Example 24, the subject matter of Example 23 optionally includes wherein the optical sensor is embedded in the return electrode.

In Example 25, the subject matter of any one or more of Examples 23-24 optionally include wherein the optical sensor is adjacent the return electrode.

In Example 26, the subject matter of any one or more of Examples 11-25 optionally include wherein the temperature sensor and the return electrode use a shared electrical conductor.

In Example 27, the subject matter of Example 26 optionally wherein the shared electrical conductor is a portion of a 1-wire EEPROM circuit.

In Example 28, the subject matter of any one or more of Examples 11-27 optionally include wherein the temperature sensor is connected to a distal tip portion of the return electrode.

In Example 29, the subject matter of any one or more of Examples 11-28 optionally include wherein the control system is configured to reduce the power delivered to the active electrode to determine a temperature of the return electrode based on the temperature signal.

In Example 30, the subject matter of any one or more of Examples 11-29 optionally include wherein the control system is configured to interrupt the power delivered to the active electrode to determine a temperature of the return electrode based on the temperature signal.

In Example 31, the subject matter of any one or more of Examples 11-30 optionally include wherein the power delivered to the active electrode is configured to treat tissue.

In Example 32, the subject matter of any one or more of Examples 11-31 optionally include wherein the power delivered to the active electrode is configured to cut tissue.

In Example 33, the subject matter of any one or more of Examples 11-32 optionally include wherein the control system is configured to reduce the power delivered to the active electrode to determine a temperature of the return electrode based on the temperature signal.

In Example 34, the subject matter of any one or more of Examples 11-33 optionally include wherein the temperature sensor is an electrical temperature sensor.

Example 35 is a surgical system for treating tissue, the system comprising: a surgical device including: an end effector including an active electrode for treating tissue; and a sensor configured to generate a data signal corresponding to a characteristic of the end effector or the tissue; and a control system operably coupled to the sensor, the control system configured to: deliver power to the active electrode; and adjust the power during a period of time that the data signal is received by the control system.

In Example 36, the subject matter of Example 35 optionally includes wherein the power delivered to the electrode is a radiofrequency energy.

In Example 37, the subject matter of any one or more of Examples 35-36 optionally include wherein the power that is delivered is returned along a common transmission line with the data signal that is received from the sensor.

In Example 38, the subject matter of any one or more of Examples 35-37 optionally include wherein the sensor comprises one or more of: a temperature sensor, a force sensor, a pressure sensor, an angle sensor, a proximity sensor, a distance sensor, an amount of tissue sensor, and a contact sensor.

In Example 39, the subject matter of any one or more of Examples 35-38 optionally include wherein the surgical device is a handheld device.

In Example 40, the subject matter of any one or more of Examples 35-39 optionally include wherein the surgical device is a robotic device.

In Example 41, the subject matter of any one or more of Examples 35-40 optionally include wherein the surgical device is any of: a hook-shaped device, a spatula, a forceps, an electrode, an electrosurgical pencil, a monopolar electrosurgical cutting instrument, a bipolar electrosurgical cutting instrument, a coagulator, or an irrigator.

In Example 42, the subject matter of any one or more of Examples 35-41 optionally include wherein the power delivered to the electrode is a radiofrequency energy.

In Example 43, the subject matter of any one or more of Examples 35-42 optionally include the end effector comprising: a return electrode configured to receive power from the tissue, the sensor and the return electrode using a shared electrical conductor.

In Example 44, the subject matter of Example 43 optionally includes wherein the shared electrical conductor is at least a portion of a 1-wire EEPROM circuit.

In Example 45, the subject matter of any one or more of Examples 43-44 optionally include the end effector comprising: an analog to digital converter (ADC) connected to the sensor and the return electrode, the ADC configured to deliver to the control system a digital signal based on the data signal.

Example 46 is a non-transitory machine-readable medium including instructions, for controlling an electrosurgical device, which when executed by a machine, cause the machine to: deliver power to an active electrode of an end effector; reduce the power delivered to the active electrode; receive a temperature signal from a temperature sensor when the power delivered to the active electrode is reduced; determine a temperature of the end effector; and adjust the delivered power based on the determined temperature.

In Example 47, the subject matter of Example 46 optionally includes wherein the power delivered to the active electrode is reduced for between 10 milliseconds and 100 milliseconds during an instance of measuring the temperature.

In Example 48, the subject matter of any one or more of Examples 46-47 optionally include the instructions to further cause the machine to: receive power from a return electrode of the end effector.

In Example 49, the subject matter of Example 48 optionally includes wherein the active electrode is connected to a first terminal of a control system, the temperature sensor is connected to a second terminal and a third terminal of the control system, and the return electrode is connected to the third terminal.

In Example 50, the subject matter of any one or more of Examples 46-49 optionally include the instructions to further cause the machine to: produce a converted temperature signal based on the temperature signal when the delivered power is reduced.

In Example 51, the subject matter of any one or more of Examples 46-50 optionally include the instructions to further cause the machine to: interrupt the power delivered to the active electrode to determine the temperature of the end effector based on the temperature signal.

Example 52 is a method of controlling an electrosurgical system, the method comprising: deliver power from a control system to an end effector to affect tissue; reduce the power delivered to the end effector; receive, from a sensor when the power delivered to the end effector is reduced, a data signal indicative of at least one characteristic of the end effector or the tissue; determine a temperature of the end effector; and adjust the delivered power based on the determined temperature.

In Example 53, the subject matter of Example 52 optionally includes wherein the control system is configured to determine a temperature of a return electrode based on the data signal generated during a period of time when the power delivered to the end effector is reduced.

In Example 54, the subject matter of any one or more of Examples 52-53 optionally include wherein the control system is configured to reduce the power delivered to the end effector for a duration between 10 milliseconds and 100 milliseconds during an instance of measuring the data signal.

In Example 55, the subject matter of any one or more of Examples 52-54 optionally include producing a converted temperature signal based on the data signal when the delivered power is reduced.

In Example 56, the subject matter of Example 55 optionally includes wherein the converted temperature signal is produced using an analog to digital converter (ADC) connected to the sensor.

In Example 57, the subject matter of any one or more of Examples 53-56 optionally include wherein the sensor and the return electrode use a shared electrical conductor.

In Example 58, the subject matter of Example 57 optionally includes wherein the shared electrical conductor is a portion of a 1-wire EEPROM circuit.

In Example 59, the subject matter of any one or more of Examples 53-58 optionally include wherein the control system is configured to reduce the power delivered to the end effector to determine a temperature of the return electrode based on the data signal.

Example 60 is a surgical system comprising: an end effector for a surgical device, the end effector comprising: an active electrode configured to deliver power to tissue; a return electrode configured to receive power from the tissue; and a temperature sensor configured to generate a temperature signal based on a temperature of the return electrode; and a control system connected to the active electrode, the return electrode, and the temperature sensor, the control system configured to adjust a power delivered to the active electrode based on the temperature signal of the return electrode.

In Example 61, the subject matter of Example 60 optionally includes wherein the control system is configured to reduce the power delivered to the active electrode while receiving the temperature signal.

In Example 62, the subject matter of any one or more of Examples 60-61 optionally include wherein the control system is configured to determine a temperature of the return electrode based on the temperature signal generated during a period of time when the power delivered to the active electrode is reduced.

In Example 63, the subject matter of any one or more of Examples 61-62 optionally include wherein the control system is configured to reduce the power delivered to the active electrode for a duration between 10 milliseconds and 100 milliseconds during an instance of measuring the temperature.

In Example 64, the subject matter of any one or more of Examples 61-63 optionally include wherein the return electrode includes a heat sink extending longitudinally between the end effector and a hand piece, the heat sink configured to transfer heat proximally away from the return electrode to cool the return electrode when the return electrode receives the power from the tissue.

In Example 65, the subject matter of any one or more of Examples 61-64 optionally include wherein a volume of the return electrode is larger than a volume of the active electrode.

In Example 66, the subject matter of Example 65 optionally includes wherein the volume of the return electrode is at least 5 times larger than the volume of the active electrode.

In Example 67, the subject matter of any one or more of Examples 60-66 optionally include wherein the temperature sensor is thermally coupled to the return electrode.

In Example 68, the subject matter of any one or more of Examples 60-67 optionally include a second return electrode, the second return electrode, the return electrode, and the active electrode and electrode extending along a longitudinal path, the return electrode and second return electrode located on laterally opposite sides of the active electrode, and an electrically insulative layer located at least partially between the active electrode and the return electrode, and located at least partially between the active electrode and the second return electrode.

Example 69 is a non-transitory machine-readable medium including instructions, for controlling an electrosurgical device, which when executed by a machine, cause the machine to: deliver power to an electrode of an end effector to affect tissue; reduce the power delivered to the end effector; receive, from an electrical sensor when the power delivered to the end effector is reduced, a data signal indicative of at least one characteristic of the end effector or the tissue being treated by the end effector, wherein the instructions cause the power delivered and the data signal received to be transmitted along a shared conductor; determine at least one characteristic based on the data signal; and adjust the delivered power based on the at least one characteristic.

In Example 70, the subject matter of Example 69 optionally includes wherein the conductor is a portion of a 1-wire EEPROM circuit.

In Example 71, the subject matter of any one or more of Examples 69-70 optionally include the instructions to further cause the machine to: determine a sensed parameter based on the data signal generated during a period of time when the power delivered to the end effector is reduced.

In Example 72, the subject matter of any one or more of Examples 69-71 optionally include the instructions to further cause the machine to: reduce the power delivered to the end effector for a duration between 10 milliseconds and 100 milliseconds during an instance of measuring the data signal.

In Example 73, the subject matter of any one or more of Examples 69-72 optionally include the instructions to further cause the machine to: produce a converted data signal when the delivered power is reduced.

In Example 74, the subject matter of Example 73 optionally includes the instructions to further cause the machine to: produce the converted data signal using an analog to digital converter (ADC) connected to the sensor.

In Example 75, the subject matter of any one or more of Examples 69-74 optionally include wherein the reduced power delivered to the end effector comprises a reduced radiofrequency energy.

In Example 76, the subject matter of any one or more of Examples 69-75 optionally include wherein the reduced power delivered to the end effector comprises a reduced voltage.

In Example 77, the subject matter of any one or more of Examples 69-76 optionally include wherein the reduced power delivered to the end effector comprises a reduced current.

In Example 78, the subject matter of any one or more of Examples 69-77 optionally include wherein the electrical sensor is a temperature sensor, and wherein the at least one characteristic is representative of the temperature of the end effector.

Example 79 is a method of controlling an electrosurgical system for treating a tissue, the method comprising: delivering power from a control system to an end effector to affect tissue; reducing the power delivered to the end effector; and receiving, from an electrical sensor when the power delivered to the end effector is reduced, a data signal indicative of at least one characteristic of the end effector or the tissue being treated by the end effector, wherein the power and the data signal are transmitted along a shared conductor.

In Example 80, the subject matter of Example 79 optionally includes wherein the shared conductor is a portion of a 1-wire EEPROM circuit.

In Example 81, the subject matter of any one or more of Examples 79-80 optionally include wherein the control system is configured to determine a sensed parameter based on the data signal generated during a period of time when the power delivered to the end effector is reduced.

In Example 82, the subject matter of any one or more of Examples 79-81 optionally include wherein the control system is configured to reduce the power delivered to the end effector for a duration between 10 milliseconds and 100 milliseconds during an instance of measuring the data signal.

In Example 83, the subject matter of any one or more of Examples 79-82 optionally include producing a converted data signal when the delivered power is reduced.

In Example 84, the subject matter of Example 83 optionally includes wherein the converted data signal is produced using an analog to digital converter (ADC) connected to the sensor.

In Example 85, the subject matter of any one or more of Examples 79-84 optionally include wherein reducing the power delivered to the end effector includes reducing a radiofrequency energy delivered to the end effector.

In Example 86, the subject matter of any one or more of Examples 79-85 optionally include wherein reducing the power delivered to the end effector includes reducing a voltage delivered to the end effector.

In Example 87, the subject matter of any one or more of Examples 79-86 optionally include wherein reducing the power delivered to the end effector includes reducing a current delivered to the end effector.

In Example 88, the subject matter of any one or more of Examples 79-87 optionally include wherein the electrical sensor is a temperature sensor, and wherein the at least one characteristic is representative of the temperature of the end effector.

Example 89 is a surgical system for treating tissue, the system comprising: a surgical device including: an end effector including an active electrode for treating tissue; and a sensor configured to generate a data signal corresponding to a characteristic of the end effector or the tissue; and a control system operably coupled to the sensor, the control system configured to: deliver power to the active electrode; and adjust the power during a period of time that the data signal is received by the control system.

In Example 90, the subject matter of Example 89 optionally includes wherein the power delivered to the electrode includes radiofrequency energy.

In Example 91, the subject matter of any one or more of Examples 89-90 optionally include wherein the power is returned along a common transmission line with the data signal that is received from the sensor.

In Example 92, the subject matter of any one or more of Examples 89-91 optionally include wherein the sensor comprises one or more of: a temperature sensor, a force sensor, a pressure sensor, an angle sensor, a proximity sensor, a distance sensor, an amount of tissue sensor, and a contact sensor.

In Example 93, the subject matter of any one or more of Examples 89-92 optionally include wherein the surgical device is a handheld device.

In Example 94, the subject matter of any one or more of Examples 89-93 optionally include wherein the surgical device is a robotic device.

In Example 95, the subject matter of any one or more of Examples 89-94 optionally include wherein the surgical device is any of: a hook-shaped device, a spatula, a forceps, an electrode, an electrosurgical pencil, a monopolar electrosurgical cutting instrument, a bipolar electrosurgical cutting instrument, a coagulator, or an irrigator.

In Example 96, the subject matter of any one or more of Examples 89-95 optionally include wherein the power delivered to the electrode includes ultra-high frequency energy.

In Example 97, the subject matter of any one or more of Examples 89-96 optionally include the end effector comprising: a return electrode configured to receive power from the tissue, the sensor and the return electrode using a shared electrical conductor.

In Example 98, the subject matter of Example 97 optionally includes wherein the shared electrical conductor is at least a portion of a 1-wire EEPROM circuit.

In Example 99, the subject matter of any one or more of Examples 97-98 optionally include the end effector comprising: an analog to digital converter (ADC) connected to the sensor and the return electrode, the ADC configured to deliver to the control system a digital signal based on the data signal.

Example 100 is a surgical system for treating tissue, the system comprising: a surgical device including: an end effector including an active electrode for treating tissue; and a sensor configured to generate a data signal corresponding to a characteristic of the end effector or the tissue; and a control system operably coupled to the sensor, the control system configured to: deliver power to the active electrode; and adjust the power during a period of time that the data signal is received by the control system.

In Example 101, the subject matter of Example 100 optionally includes wherein the power delivered to the electrode includes radiofrequency energy or ultra-high frequency energy.

In Example 102, the subject matter of any one or more of Examples 100-101 optionally include wherein the control system is configured to reduce the power delivered to the end effector for a duration between 10 milliseconds and 100 milliseconds during an instance of measuring the data signal.

In Example 103, the subject matter of any one or more of Examples 100-102 optionally include wherein the power is returned along a common transmission line with the data signal that is received from the sensor.

In Example 104, the subject matter of any one or more of Examples 100-103 optionally include wherein the sensor comprises one or more of: a temperature sensor, a force sensor, a pressure sensor, an angle sensor, a proximity sensor, a distance sensor, an amount of tissue sensor, and a contact sensor.

In Example 105, the subject matter of any one or more of Examples 100-104 optionally include wherein the surgical device is a handheld device in particular a hook-shaped device, a spatula, a forceps, an electrode, an electrosurgical pencil, a monopolar electrosurgical cutting instrument, a bipolar electrosurgical cutting instrument, a coagulator, or an irrigator.

In Example 106, the subject matter of any one or more of Examples 100-105 optionally include wherein the surgical device is a robotic device.

In Example 107, the subject matter of any one or more of Examples 100-106 optionally include the end effector comprising: a return electrode configured to receive power from the tissue, the sensor and the return electrode using a shared electrical conductor.

In Example 108, the subject matter of Example 107 optionally includes wherein the shared electrical conductor is at least a portion of a 1-wire EEPROM circuit.

In Example 109, the subject matter of any one or more of Examples 107-108 optionally include the end effector comprising: an analog to digital converter (ADC) connected to the sensor and the return electrode, the ADC configured to deliver to the control system a digital signal based on the data signal.

Example 110 is a method of controlling the surgical system of any of Examples 100-109, the method comprising: delivering power from a control system to an end effector to affect tissue; reducing the power delivered to the end effector; and receiving, from an electrical sensor when the power delivered to the end effector is reduced, a data signal indicative of at least one characteristic of the end effector or the tissue being treated by the end effector, wherein the power and the data signal are transmitted along a shared conductor.

In Example 111, the subject matter of Example 110 optionally includes wherein the control system is configured to determine a sensed parameter based on the data signal generated during a period of time when the power delivered to the end effector is reduced.

In Example 112, the subject matter of any one or more of Examples 110-111 optionally include wherein the control system is configured to reduce the power delivered to the end effector for a duration between 10 milliseconds and 100 milliseconds during an instance of measuring the data signal.

In Example 113, the subject matter of any one or more of Examples 110-112 optionally include producing a converted data signal when the delivered power is reduced.

In Example 114, the subject matter of Example 113 optionally includes wherein the converted data signal is produced using an analog to digital converter (ADC) connected to the sensor.

In Example 115, the subject matter of any one or more of Examples 110-114 optionally include wherein reducing the power delivered to the end effector includes reducing a radiofrequency energy, a voltage or a current delivered to the end effector.

Example 116 is at least one machine-readable medium including instructions that, when executed by processing circuitry, cause the processing circuitry to perform operations to implement of any of Examples 1-115.

Example 117 is an apparatus comprising means to implement of any of Examples 1-115.

Example 118 is a system to implement of any of Examples 1-115.

Example 119 is a method to implement of any of Examples 1-115.

In Example 120, the apparatuses or method of any one or any combination of Examples 1-119 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A surgical system comprising:
a surgical device comprising:
    a hand piece operable to control the surgical device; and
    an end effector connected to the hand piece, the end effector comprising:
        an active electrode configured to deliver power to tissue, the active electrode connected to a first terminal of a control system;
        a return electrode configured to receive power from the tissue, the return electrode connected to a third terminal of the control system; and
        a temperature sensor configured to generate a temperature signal based on a temperature of the return electrode, the temperature sensor connected to a second terminal of the control system and the third terminal of the control system; and
    wherein the control system is connected to the active electrode, the return electrode, and the temperature sensor, wherein the control system configured to adjust a power delivered to the active electrode based on the temperature signal of the return electrode, and wherein the control system is configured to reduce the power delivered to the active electrode while receiving the temperature signal.

2. The surgical system of claim 1, wherein the control system is configured to determine a temperature of the return electrode based on the temperature signal generated during a period of time when the power delivered to the active electrode is reduced.

3. The surgical system of claim 1, wherein the control system is configured to reduce the power delivered to the active electrode for a duration between 10 milliseconds and 100 milliseconds during an instance of measuring the temperature.

4. The surgical system of claim 1, wherein the return electrode includes a heat sink extending longitudinally between the end effector and the hand piece, the heat sink configured to transfer heat proximally away from the return electrode to cool the return electrode when the return electrode receives the power from the tissue.

5. The surgical system of claim 4, wherein a volume of the return electrode is larger than a volume of the active electrode.

6. The surgical system of claim 1, wherein the temperature sensor is thermally coupled to the return electrode.

7. The surgical system of claim 1, comprising:
a second return electrode, the second return electrode, the return electrode, and the active electrode and electrode extending along a longitudinal path, the return electrode and second return electrode located on laterally opposite sides of the active electrode, and
an electrically insulative layer located at least partially between the active electrode and the return electrode, and located at least partially between the active electrode and the second return electrode.

8. The surgical system of claim 1, comprising:
a converter located at least partially within the surgical device and connected to the second terminal and the third terminal, the converter configured to produce a converted temperature signal based on the temperature signal when the delivered power is reduced.

9. The surgical system of claim 1, wherein the temperature sensor and the return electrode use a shared electrical conductor.

10. The surgical system of claim 9, wherein the shared electrical conductor is a portion of a 1-wire EEPROM circuit.

11. The surgical system of claim 1, wherein the control system is configured to interrupt the power delivered to the active electrode to determine a temperature of the return electrode based on the temperature signal.

12. A non-transitory machine-readable medium including instructions, for controlling an electrosurgical device, which when executed by a machine, cause the machine to:
deliver power to an active electrode of an end effector, the active electrode connected to a first terminal of a control system;
reduce the power delivered to the active electrode;
receive a temperature signal from a temperature sensor when the power delivered to the active electrode is reduced, the temperature sensor connected to a second terminal and a third terminal of the control system;
determine a temperature of the end effector;
receive power from a return electrode of the end effector, the return electrode connected to the third terminal; and
adjust the delivered power based on the determined temperature.

13. The non-transitory machine-readable medium of claim 12, wherein the power delivered to the active electrode is reduced for between 10 milliseconds and 100 milliseconds during an instance of measuring the temperature.

14. The non-transitory machine-readable medium of claim 12, the instructions to further cause the machine to:
produce a converted temperature signal based on the temperature signal when the delivered power is reduced.

15. The non-transitory machine-readable medium of claim 12, the instructions to further cause the machine to:
interrupt the power delivered to the active electrode to determine the temperature of the end effector based on the temperature signal.

16. A non-transitory machine-readable medium including instructions, for controlling an electrosurgical device, which when executed by a machine, cause the machine to:
deliver power to an electrode of an end effector to affect tissue;
reduce the power delivered to the end effector after delivering power to the electrode;
receive, from an electrical sensor when the power delivered to the end effector is reduced, a data signal indicative of at least one characteristic of the end effector, wherein the instructions cause the power delivered and the data signal received to be transmitted along a shared conductor, wherein the shared conductor is a portion of a 1-wire EEPROM circuit;
determine the at least one characteristic based on the data signal, the at least one characteristic including a temperature of the end effector; and
adjust the delivered power based on the at least one characteristic.

17. The non-transitory machine-readable medium of claim 16, the instructions to further cause the machine to:
determine a sensed parameter based on the data signal generated during a period of time when the power delivered to the end effector is reduced.

18. The non-transitory machine-readable medium of claim 16, the instructions to further cause the machine to:
reduce the power delivered to the end effector for a duration between 10 milliseconds and 100 milliseconds during an instance of measuring the data signal.

19. The non-transitory machine-readable medium of claim 16, the instructions to further cause the machine to:
produce a converted data signal when the delivered power is reduced.

20. The non-transitory machine-readable medium of claim 16, wherein the reduced power delivered to the end effector comprises one or more of a reduced radiofrequency energy, a reduced voltage, and a reduced current.

* * * * *